US006815451B2

(12) United States Patent
Velker et al.

(10) Patent No.: US 6,815,451 B2
(45) Date of Patent: Nov. 9, 2004

(54) 1,2,3,4-TETRAHYDROISOQUINOLINES DERIVATIVES AS UROTENSIN II RECEPTOR ANTAGONISTS

(75) Inventors: Jörg Velker, Lörrach (DE); Hamed Aissaoui, Wittenheim (FR); Christoph Binkert, Basel (CH); Martine Clozel, Binningen (CH); Boris Mathys, Egerkingen (CH); Claus Mueller, Hegenheim (FR); Oliver Nayler, Arlesheim (CH); Michael Scherz, Ettingen (CH); Thomas Weller, Binningen (CH)

(73) Assignee: Actelion Pharmaceuticals Ltd. (CH)

( * ) Notice: Subject to any disclaimer, the term of this patent is extended or adjusted under 35 U.S.C. 154(b) by 0 days.

(21) Appl. No.: 10/471,724

(22) PCT Filed: Mar. 20, 2002

(86) PCT No.: PCT/EP02/03131

§ 371 (c)(1),
(2), (4) Date: Sep. 15, 2003

(87) PCT Pub. No.: WO02/076979

PCT Pub. Date: Oct. 3, 2002

(65) Prior Publication Data

US 2004/0110744 A1 Jun. 10, 2004

(30) Foreign Application Priority Data

Mar. 27, 2001 (EP) ................................. 0103422
Aug. 27, 2001 (EP) ................................. 0109845

(51) Int. Cl.$^7$ ...................... C07D 403/12; A61K 31/47
(52) U.S. Cl. .................. 514/300; 514/217.04; 514/307; 514/314; 540/593; 546/113; 546/135; 546/148
(58) Field of Search ........................... 514/217.04, 300, 514/307, 314; 540/593; 546/113, 135, 148

(56) References Cited

U.S. PATENT DOCUMENTS 5,317,020 A    5/1994   Emonds-Alt et al.

FOREIGN PATENT DOCUMENTS

| EP | 0 501 693 A1 | 9/1992 |
| EP | 0 428 434 A2 | 5/1994 |
| WO | WO 99/21835 | 5/1999 |
| WO | WO 01/09088 A1 | 2/2001 |
| WO | WO 01/45694 A1 | 6/2001 |
| WO | WO 01/45700 A1 | 6/2001 |
| WO | WO 01/45711 A1 | 6/2001 |
| WO | WO 02/00606 A1 | 1/2002 |
| WO | WO 02/02530 A1 | 1/2002 |

OTHER PUBLICATIONS

Ames R.S. et al., "Human Urotensin–II is a Potent Vasoconstrictor and Agonist for the Orphan Receptor GPR14", *Nature*, vol. 401, Sep. 16, 1999, pp. 282–286.

Barlin G.B. and Tan Weng–Lai, "Potential Antimalarials. I 1,8–Naphthyridines", *Australian Journal of Chemistry*, vol. 37, 1984, pp. 1065–1073.

Bern H.A. et al., "Neurohormones from Fish Tails: The Caudal Neurosecretory System I. "Urophysiology" and the Caudal Neurosecretory System of Fishes", *Recent Progress in Hormone Research*, vol. 41, 1985, pp. 533–552.

Brasyunas V.B. et al., "Synthesis of Quinoline–4–Carboxylic Acid and Its Derivatives", in *Chemistry of Heterocyclic Compounds*, vol. 24, No. 6, Jun. 1988, pp. 670–672.

Breu V. et al., "In Vitro Characterization of Ro 46–2005, a Novel Synthetic Non–Peptide Endothelin Antagonist of $ET_a$ and $ET_b$ Receptors", *Federation of European Biochemical Societies*, vol. 334, No. 2, Nov. 1993, pp. 210–214.

Douglas S.A. et al., "Differential Vasoconstrictor Activity of Human Urotensin–II in Vascular Tissue Isolated from the Rat, Mouse, Dog, Pig, Marmoset and Cynomolgus Monkey", *British Journal of Pharmacology*, vol. 131, No. 7, 2000, pp. 1262–1274.

Douglas S.A. et al., "Human Urotensin–II is a Potent Vasoactive Peptide: Pharmacological Characterization in the Rat, Mouse, Dog and Primate", *Journal of Cardiovascular Pharmacology*, vol. 36 (Supp. 1), 2000, pp. S163–S166.

Finkelstein J. et al., Synthesis of 1,2,3,4–Tetrahydro–1,1,2,3,3,4,4–heptamethyl–6,7–dimethoxyisoquinoline and Related Compounds as Potential Hypotensive Agents, *Journal of Medicinal Chemistry*, vol. 14, No. 7, 1971, pp. 584–588.

Garlton J. et al., "Central Effects of Urotensin–II following ICV Andministration in Rats", *Psychopharmacology*, 2001, vol. 155, pp. 426–433.

Liu Q. et al., "Identification of Urotensin II as the Endogenous Ligand for the Orphan G–Protein–Coupled Receptor GPR14", *Biochemical and Biophysical Research Communications*, vol. 226, No. 1, 1999, pp. 174–178.

Mori M. et al., "Urotensin II Is the Endogenous Ligand of a G–Protein–Coupled Orphan Receptor, SENR (GPR14)", *Biochemical and Biophysical Research Communications*, vol. 265, No. 1, 1999, pp.123–129.

Polniaszek R.P. and Kaufman C.R., "Stereoselective Nucleophilic Additions to the Carbon–Nitrogen Double Bond. 2. Chiral Iminium Ions Derived from "Second Generation" Chiral Amines", *Journal of American Chemical Society*, vol. 111(13), 1989, pp. 4859–4863.

(List continued on next page.)

*Primary Examiner*—Zinna Northington Davis
(74) *Attorney, Agent, or Firm*—Dickstein, Shapiro, Morin & Oshinsky, LLP.

(57) ABSTRACT

The invention relates to novel 1,2,3,4-tetrahydroisoquinoline derivatives of formula (I) and related compounds and their use as active ingredients in the preparation of pharmaceutical compositions. The invention also concerns related aspects including processes for the preparation of the compounds, pharmaceutical compositions containing one or more of those compounds and especially their use as neurohormonal antagonists especially urotensin II antagonists.

18 Claims, No Drawings

OTHER PUBLICATIONS

Radinov R. et al., "Synthesis of 4–Amino–3–pyridinyl and 4–Amino–5–pyrimidinyl Aryl Ketones and Related Compounds via an ortho–Lithiation Reaction", *Papers,* Nov. 1986, pp. 886–891.

Russell F.D. et al., "Cardiostimulant Effects of Urotensin–II in Human Heart in vitro", *British Journal of Pharmacology,* vol. 132, 2001, pp. 5–9.

Russell R.K., "Thiophene Systems. 9. Thienopyrimidinedione Derivatives as Potential Antihypertensive Agents", *Journal of Medicinal Chemistry,* vol. 31, No. 9, 1988, pp. 1786–1793.

Shinkai H. et al., "4–Aminoquinolines: Novel Nociceptin Antagonists with Analgesic Activity", *Journal of Medicinal Chemistry,* vol. 43, No. 24, 2000, pp. 4667–4677.

Silvestre R.A. et al., "Inhibition of Insulin Release by Urotensin II–A Study on the Perfused Rat Pancreas", *Horm. Metab. Res.,* vol. 33, 2001, pp. 379–381.

Takahashi K. et al., "Expression of Urotensin II and Urotensin II Receptor mRNAs in Various Human Turmor Cell Lines and Secretion of Urotensin II–like Immunoreactivity by SW–13 Adrenocortical Carcinoma Cells", *Peptides,* 2001, vol. 22, pp. 1175–1179.

Totsune K. et al., "Role of Urotensin II in Patients On Dialysis", *The Lancet,* vol. 358, Sep. 8, 2001, p. 810–811.

Tzanidis A. et al. "Urotensin II Stimulates Collagen Synthesis by Cardiac Fibroblasts and Hypertrophic Signalling in Cardiomyocytes via G(alpha)q– and Ras–Dependent Pathways", *JACC,* Abstract No. 822–5, Feb. 2001.

Ukaji Y. et al., "Catalytic Asymmetric Addition of Dialkylzinc to 3,4–Dihydroisoquinoline N– Oxides Utilizing Tartaric Acid Ester as a Chiral Auxiliary", *Bulletin of the Chemical Society of Japan,* vol. 73, No. 2, 2000, pp. 447–452.

Whaley W.M. and Govindachari T.R., "The Preparation of 3,4–Dihydroisoquinolines and Related Compounds by the Bischler–Napieralski Reaction", *Synthesis of Isoquinolines,* University of Illinois, Chapter 2, pp. 74–150.

Zheng W. et al., "2–Amino–4–benzyl–4,5,6,7–tetrahydrothiazolo[5,4–c]pyridines: Novel Selective $\beta_3$–Adrenoceptor Agonists", *Journal of Medicinal Chemistry,* vol. 42, No. 12, 1999, pp. 2287–2294.

Zou Y. et al., "Urotensin II Induces Hypertrophic Responses in Cultured Cardiomyocytes from Neonatal Rats", *FEBS Letters,* Elsevier Science B.V., 2001, vol. 508, pp. 57–60.

Copy of International Search Report for PCT/EP02/03131.

1,2,3,4-TETRAHYDROISOQUINOLINES DERIVATIVES AS UROTENSIN II RECEPTOR ANTAGONISTS

FIELD OF THE INVENTION

The present invention relates to novel 1,2,3,4-tetrahydroisoquinoline derivatives of the general formula 1 and their use as active ingredients in the preparation of pharmaceutical compositions. The invention also concerns related aspects including processes for the preparation of the compounds, pharmaceutical compositions containing one or more compounds of the general formula 1 and especially their use as neurohormonal antagonists.

BACKGROUND OF THE INVENTION

Urotensin II is a cyclic 11-amino acid peptide that has some sequence similarity to, but is not homologous with, somatostatin-14. Urotensin II was first isolated and sequenced from fish spinal cord (Bern H A, Pearson D, Larson B A, Nishioka R S. Neurohormones from fish tails: the caudal neurosecretory system. I. "Urophysiology" and the caudal neurosecretory system of fishes. Recent Prog. Horm. Res. (1985) 41, 533–552), and has since been found in a wide variety of vertebrate and invertebrate species. Human urotensin II is synthesized in a prepro-form from a single gene located at chromosome 1p36.21, and two cDNA splice variants which differ in their putative signal peptide sequence have been isolated from human colon tumor and human placenta (GenBank Accession Nr. O95399). The putative prohormone convertase dibasic cleavage site is strictly conserved across species. The mature 11-amino acid peptide contains a C-terminal disulfide-bridged 6-amino acid loop which is also strictly conserved, while the N-terminal portion of the mature cyclic peptide can vary considerably across species.

Urotensin II exerts potent and complex hemodynamic actions in mammals (Douglas S A, Sulpizio A C, Piercy V, Sarau H M, Ames R S, Alyar N V, Ohlstein E H, Willette R N. "Differential vasoconstrictor activity of human urotensin-II in vascular tissue isolated from the rat, mouse, dog, pig, marmoset and cynomolgus monkey." Br. J. Pharmacol. (2000) 131, 1262–1274. Douglas, S A, Ashton D J, Sauermelch C F, Coatney R W, Ohlstein D H, Ruffolo M R, Ohlstein E H, Alyar N V, Willette R "Human Urotensin-II is a potent vasoactive peptide: pharmacological characterization in the rat, mouse, dog and primate." J. Cardiovasc. Pharmacol. (2000) 36, Suppl 1:S163–6). The peptide effectively constricts isolated mammalian arteries. The potency of vasoconstriction is an order of magnitude greater than that of endothelin-1. These effects appear to be mediated at least in part via the actions of urotensin II on a G-protein coupled receptor named GPR-14 or SENR (Ames R S, et al. "Human urotensin-II is a potent vasoconstrictor and agonist for the orphan receptor GPR14." Nature. (1999) 401, 282–6. Mori M, Sugo T, Abe M, Shimomura Y, Kurihara M, Kitada C, Kikuchi K, Shintani Y, Kurokawa T, Onda H, Nishimura 0, Fujino M. "Urotensin II is the endogenous ligand of a G-protein-coupled orphan receptor, SENR (GPR14)" Biochem. Biophys. Res. Commun. (1999) 265, 123–9. Liu Q, Pong S S, Zeng Z, et al. "Identification of urotensin II as the endogenous ligand for the orphan G-protein-coupled receptor GPR14" Biochem. Biophys. Res. Commun. (1999) 266, 174–178.) GPR14 is expressed in arterial (but not venous) smooth muscle cells, on atrial and ventricular cardiac myocytes, in pancreas, kidney, and in the brain.

In addition to its vasoconstrictive actions, urotensin II potently affects atrial and ventricular muscle contraction (Russell F D, Molenaar P, and O'Brien D M "Cardiostimulant effects of urotensin-II in human heart in vitro". Br J Pharmacol (2001) 132, 5–9).

Urotensin II stimulates cellular proliferation, migration and collagen synthesis in cardiac fibroblasts (Tzandis A, et al., "Urotensin II stimulates collagen synthesis by cardiac fibroblasts and hypertrophic signaling cardiomyocytes via G(alpha)q- and Ras-dependent pathways". J. Am. Coll. Cardiol. (2001) 37, 164A.) and in neonatal myocytes (Zou Y, Nagai R, and Yamazaki T, "Urotensin II induces hypertrophic responses in cultured cardiomyocytes from neonatal rats". FEBS Lett (2001) 508, 57–60). Urotensin II is produced by cancer cell lines and its receptor is also expressed in these cells. (Takahashi K, et al., "Expression of urotensin II and urotensin II receptor mRNAs in various human tumor cell lines and secretion of urotensin II-like immunoreactivity by SW-13 adrenocortical carcinoma cells". Peptides (2001) 22, 1175–9).

Urotensin II modulates' glucose-stimulated pancreatic release of insulin (Silvestre R A, et al., "Inhibition of insulin release by urotensin II—a study on the perfused rat pancreas". Horm Metab Res (2001) 33, 379–81).

Elevated circulating levels of urotensin II are detected in humans susceptible to high-altitude pulmonary edema, and in patients awaiting kidney transplantation (Totsune K, et al., "Role of urotensin II in patients on dialysis". Lancet (2001) 358, 810–1).

Urotensin II and its receptor are found in spinal cord and brain tissue, and intracerebroventricular infusion of urotensin II into mice induces behavioral changes (Gartlon J, et al., "Central effects of urotensin-II following ICV administration in rats". Psychopharmacology (Berlin) (2001) 155, 426–33).

Substances with the ability to block the actions of urotensin II are accordingly expected to prove useful in the treatment of various diseases. WO-2001/45694 discloses certain sulfonamides as urotensin II receptor antagonists, and their use to treat diseases associated with a urotensin II imbalance. WO-2001/45700 discloses certain pyrrolidines as urotensin II receptor antagonists and their use to treat diseases associated with a urotensin II imbalance. WO-2001/45711 discloses certain pyrrolyl and pyridyl derivatives as urotensin II receptor antagonists and their use to treat diseases associated with a urotensin II imbalance. WO-2002/00606 discloses certain biphenyl compounds useful as urotensin II receptor antagonists, and WO-2002/02530 also discloses certain compounds useful as urotensin II receptor antagonists.

The present invention comprises 1,2,3,4-tetrahydroisoquinoline derivatives which are novel compositions of matter and which are urotensin II receptor antagonists. EP 428434 discloses certain alkylureidopyridines as neurokinin and substance P antagonists. WO-99/21835 discloses certain ureidoquinolines as H+-ATPase and bone resorption inhibitors. WO-01/009088 discloses certain substituted heteroarylureas as inhibitors of the CCR-3 receptor.

DESCRIPTION OF THE INVENTION

The present invention relates to compounds of the general formula 1,

General Formula 1

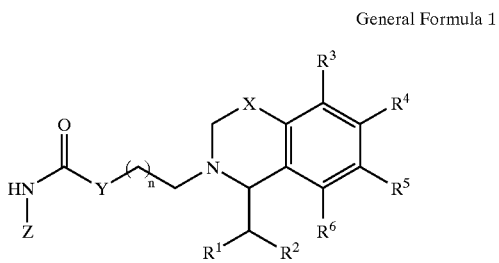

wherein

X represents —$CH_2$—, —$CH_2CH_2$—, —$C(CH_3)_2$—;

Y represents oxygen, NH;

n represents the numbers 1 or 2;

Z represents quinolin-4-yl which may be mono-substituted with lower alkyl in the positions 2, 6, or 8, or di-substituted with lower alkyl in the positions 2, 6 or 2,8; [1,8]naphthyridin-4-yl which may be substituted in position 7 with lower alkyl; pyridin-4-yl which may be substituted in position 2 with $R^7R^8N$— and additionally in position 6 with hydrogen or lower alkyl;

$R^1$ represents naphthalen-1-yl; naphthalen-2-yl; benzo[1,3]dioxol-5-yl; benzyl, or mono-, di-, or tri-substituted benzyl substituted in the phenyl ring independently with lower alkyl, lower alkyloxy, trifluoromethyl, halogen, cyano; phenyl, or mono-, di- or tri-substituted phenyl, substituted independently with lower alkyl, lower alkyloxy, trifluoromethyl, halogen, cyano;

$R^2$ represents hydrogen, lower alkyl, aryl or forms with $R^1$ a styryl group of E or Z geometry, whereby the phenyl ring in the styryl group may be mono-, di- or tri-substituted phenyl, substituted independently with lower alkyl, lower alkyloxy, trifluoromethyl, halogen, cyano;

$R^3$, $R^4$, $R^5$ and $R^6$ independently represent hydrogen, cyano, hydroxy, lower alkyloxy, aralkyloxy, lower alkenyloxy, and $R^5$ additionally represents $R^7R^8NCO$;

$R^4$ and $R^5$ together may form with the phenyl ring a five- or a six-membered ring containing one or two oxygen atoms;

$R^7$ and $R^8$ independently represent hydrogen, lower alkyl, aryl, aralkyl, or together with the N form a pyrrolidine, piperidine, or morpholine ring;

and optically pure enantiomers or diastereomers, mixtures of enantiomers or diastereomers, diastereomeric racemates, and mixtures of diastereomeric racemates; as well as their pharmaceutically acceptable salts, solvent complexes, and morphological forms.

In the definitions of the general formula 1 the expression 'lower alkyl' means straight or branched chain groups with one to seven carbon atoms, preferably 1 to 4 carbon atoms; or cyclic alkyl groups with three to six carbon atoms. Preferred examples of lower alkyl groups are methyl, ethyl, n-propyl, isopropyl, n-butyl, iso-butyl, sec-butyl, tert-butyl, n-pentyl, n-hexyl, n-heptyl, cyclopropyl, cyclobutyl, cyclopentyl, or cyclohexyl.

The expression 'lower alkyloxy' means a group of the formula lower alkyl-O— in which the term 'lower alkyl' has the meaning previously given. Preferred examples of lower alkyloxy groups are methoxy, ethoxy, propoxy, iso-propoxy, butoxy, iso-butoxy, sec-butoxy, tert-butoxy, cyclopentyloxy, and cyclohexyloxy.

The expression 'lower alkenyloxy' means a group of the formula lower alkenyl-O— in which the term 'lower alkenyl' means a straight-chain or branched-chain alkenyl group with 2 to 5 carbon atoms. Preferred examples of lower alkenyloxy groups are allyloxy or propenyloxy.

The expression 'aryl' means a phenyl or naphthyl group which optionally carries one or more substituents, preferably one or two substituents, each independently selected from cyano, halogen, lower alkyl, lower alkenyl, lower alkyloxy, lower alkenyloxy, trifluoromethyl, trifluoromethoxy, amino, carboxy and the like. Preferred examples of aryl groups are phenyl, 4-methylphenyl, 4-methoxyphenyl, 4-cyanophenyl, 4-chlorophenyl, 4-fluorophenyl, 2-methylphenyl, 2-chlorophenyl, 2-fluorophenyl, 2-methoxyphenyl, naphthalen-1-yl and naphthalen-2-yl.

The expression 'alkyloxy' means a lower alkyl group as previously defined in which one hydrogen atom has been replaced by an aryl group as previously defined. Preferred examples of aralkyl groups are benzyl and benzyl substituted in the phenyl ring with hydroxy, lower alkyl, lower alkyloxy or halogen.

The expression 'aralkyloxy' means a group of the formula aralkyl-O— in which the term 'aralkyl' has the meaning previously given. Preferred examples of aralkyloxy are benzyloxy and phenethyloxy.

The present invention encompasses pharmaceutically acceptable salts of compounds of the general formula 1. This encompasses either salts with inorganic acids or organic acids like hydrohalogenic acids, e.g. hydrochloric or hydrobromic acid, sulfuric acid, phosphoric acid, nitric acid, citric acid, formic acid, acetic acid, maleic acid, tartaric acid, methylsulfonic acid, p-tolylsulfonic acid and the like or in case the compound of formula 1 is acidic in nature with an inorganic base like an alkali or earth alkali base, e.g. sodium, potassium, or calcium salts, etc.

The present invention encompasses different solvation complexes of compounds of general formula 1. The solvation can be effected in the course of the manufacturing process or can take place separately, e.g. as a consequence of hygroscopic properties of an initially anhydrous compound of general formula 1.

The present invention further encompasses different morphological forms, e.g. crystalline forms, of compounds of general formula 1 and their salts and solvation complexes. Particular heteromorphs may exhibit different dissolution properties, stability profiles, and the like, and are all included in the scope of the present invention.

The compounds of the general formula 1 might have one or more asymmetric carbon atoms and may be prepared in form of optically pure enantiomers or diastereomers, mixtures of enantiomers or diastereomers, diastereomeric racemates, and mixtures of diastereomeric racemates. The present invention encompasses all these forms. They are prepared by stereoselective synthesis, or by separation of mixtures in a manner known per se, i.e. by column chromatography, thin layer chromatography, HPLC, crystallization, etc.

Preferred compounds of general formula 1 are the compounds of general formula 2, General Formula 2

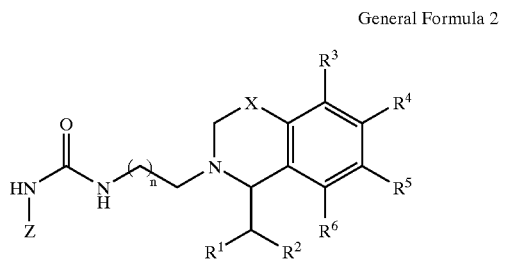

wherein R¹, R², R³, R⁴, R⁵, R⁶, X, Z, and n have the meaning given in general formula 1 above.

Another group of preferred compounds of general formula 1 are the compounds of general formula 3, General Formula 3

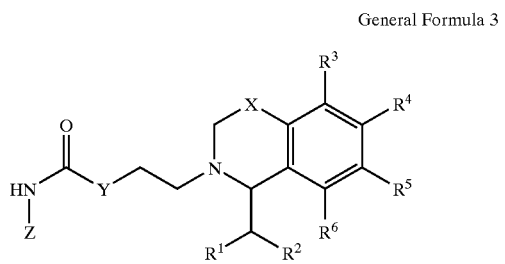

wherein R¹, R², R³, R⁴, R⁵, R⁶, X, Y, and Z have the meaning given in general formula 1 above.

Another group of preferred compounds of general formula 1 are the compounds of general formula 4, General Formula 4

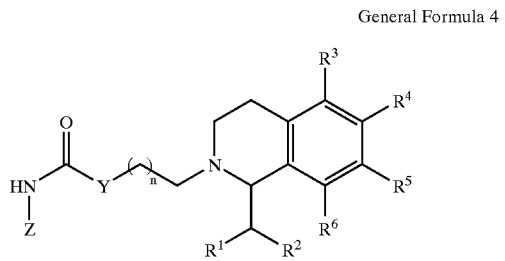

wherein R¹, R², R³, R⁴, R⁵, R⁶, Y, Z, and n have the meaning given in general formula 1 above.

Another group of preferred compounds of general formula 1 are the compounds of general formula 5, General Formula 5

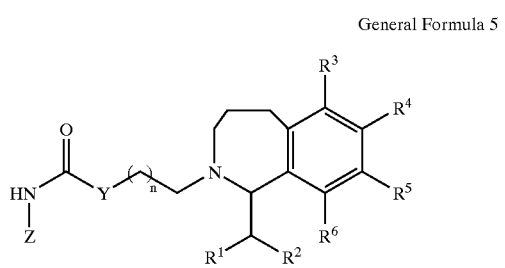

wherein R¹, R², R³, R⁴, R⁵, R⁶, Y, Z, and n have the meaning given in general formula 1 above.

Another group of preferred compounds of general formula 1 are the compounds of general formula 6, General Formula 6

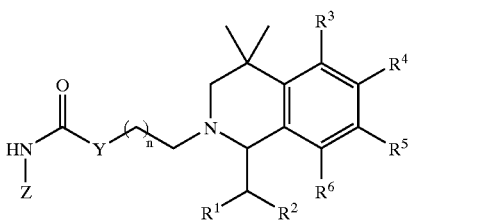

wherein R¹, R², R³, R⁴, R⁵, R⁶, Y, Z, and n have the meaning given in general formula 1 above.

Another group of preferred compounds of general formula 1 are the compounds of general formula 7, General Formula 7

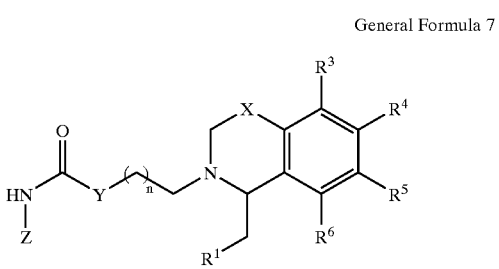

wherein R¹, R³, R⁴, R⁵, R⁶, X, Y, Z, and n have the meaning given in general formula 1 above.

Another group of preferred compounds of general formula 1 are the compounds of general formula 8, General Formula 8

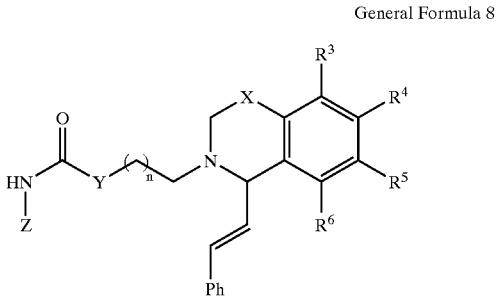

wherein Ph is phenyl; mono-, di- or tri-substituted phenyl, substituted independently with hydrogen, lower alkyl, lower alkyloxy, trifluoromethyl, halogen, or cyano; and R³, R⁴, R⁵, R⁶, X, Y, Z, and n have the meaning given in general formula 1 above.

Another group of preferred compounds of general formula 1 are the compounds of general formula 9, General Formula 9

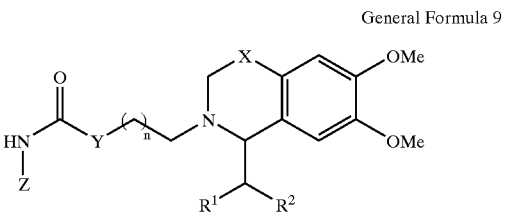

wherein R¹, R², X, Y, Z, and n have the meaning given in general formula 1 above.

Another group of preferred compounds of general formula 1 are the compounds of general formula 10, General Formula 10

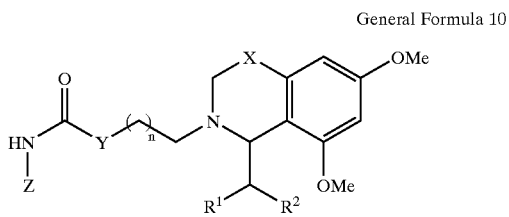

wherein $R^1$, $R^2$, X, Y, Z, and n have the meaning given in general formula 1 above.

Another group of preferred compounds of general formula 1 are the compounds of general formula 11, General Formula 11

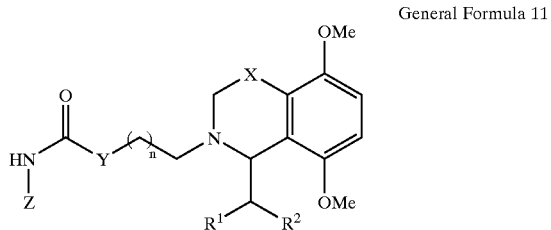

wherein $R^1$, $R^2$, X, Y, Z, and n have the meaning given in general formula 1 above.

Another group of preferred compounds of general formula 1 are the compounds of general formula 12, General Formula 12

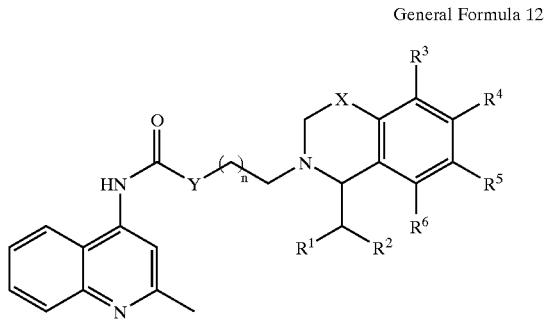

wherein $R^1$, $R^2$, $R^3$, $R^4$, $R^5$, $R^6$, X, Y, and n have the meaning given in general formula 1.

Another group of preferred compounds of general formula 1 are the compounds of general formula 13, General Formula 13

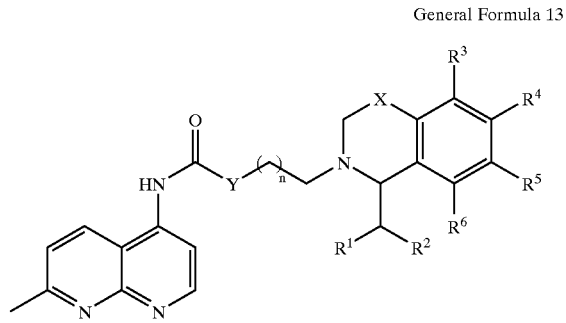

wherein $R^1$, $R^2$, $R^3$, $R^4$, $R^5$, $R^6$, X, Y, and n have the meaning given in general formula 1.

Another group of preferred compounds of general formula 1 are the compounds of general formula 14, General Formula 14

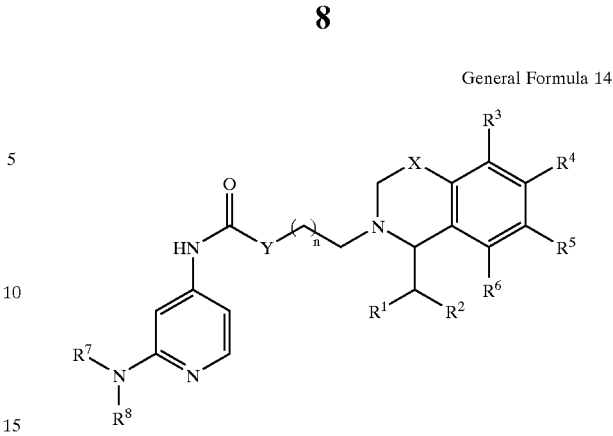

wherein $R^1$, $R^2$, $R^3$, $R^4$, $R^5$, $R^6$, $R^7$, $R^8$, X, Y, and n have the meaning given in general formula 1.

Another group of preferred compounds of general formula 1 are the compounds of general formula 15, General Formula 15

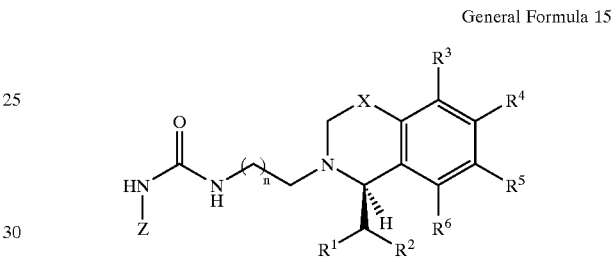

wherein the 1 position of the 1,2,3,4-tetrahydroisoquinoline ring system has the R absolute stereochemical configuration, and $R^1$, $R^2$, $R^3$, $R^4$, $R^5$, $R^6$, X, Z, and n have the meaning given in general formula 1.

Another group of preferred compounds of general formula 1 are the compounds of general formula 16, General Formula 16

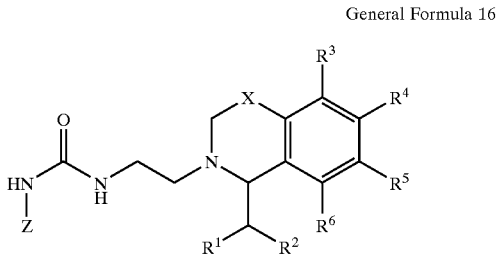

wherein $R^3$, $R^4$, $R^5$, and $R^6$ are independently hydrogen or lower alkyloxy; and $R^1$, $R^2$, and Z have the meaning given in general formula 1 above.

Examples of particularly preferred compounds of general formula 1 are:

1-{2-[1-(4-Fluoro-benzyl)-6,8-dimethoxy-3,4-dihydro-1H-isoquinolin-2-yl]-ethyl}-3-(2-methyl-quinolin-4-yl)-urea 1-{2-[1-(3,4-Difluoro-benzyl)-6,8-dimethoxy-3,4-dihydro-1H-isoquinolin-2-yl]-ethyl}-3-(2-methyl-quinolin-4-yl)-urea 1-{2-[1-(3-Fluoro-4-methoxy-benzyl)-6,8-dimethoxy-3,4-dihydro-1H-isoquinolin-2-yl]-ethyl}-3-(2-methyl-quinolin-4-yl)-urea 1-{2-[1-(3,4-Difluoro-benzyl)-6,8-dimethoxy-3,4-dihydro-1H-isoquinolin-2-yl]-ethyl}-3-quinolin-4-yl-urea 1-{2-[1-(3-Fluoro-4-methoxy-benzyl)-6,8-dimethoxy-3,4-dihydro-1H-isoquinolin-2-yl]-ethyl}-3-quinolin-4-yl-urea 1-{2-[1-(4-Fluoro-benzyl)-6,8-dimethoxy-3,4-dihydro-1H-isoquinolin-2-yl]-ethyl}-3-quinolin-4-yl-urea 1-(2-{1-[2-(4-Fluoro-phenyl)ethyl]-6,8-dimethoxy-3,4-dihydro-1H-isoquinolin-2-yl}-ethyl)-3-(2-methyl-quinolin-4-yl)-urea 1-(2-{1-[2-(2,4-Difluoro-phenyl)-ethyl]-6,8-dimethoxy-3,4-dihydro-1H-isoquinolin-2-yl}-ethyl-3-(2-methyl-quinolin-4-yl)-urea 1-(2-{1-[2-(2,4-Difluoro-phenylpethyl]-6,8-dimethoxy-3,4-dihydro-1H-isoquinolin-2-yl}-ethyl)-3-quinolin-4-yl-urea 1-(2-{1-[2-(3,4-Difluoro-phenyl)-ethyl]-6,8-dimethoxy-3,4-dihydro-1H-isoquinolin-2-yl}-ethyl)-3-(2-methyl-quinolin-4-yl)-urea 1-(2-{1-[2-(3,4-Difluoro-phenyl)-ethyl]-6,8-dimethoxy-3,4-dihydro-1H-isoquinolin-2-yl}-ethyl)-3-quinolin-4-yl-urea 1-(2-{1-[2-(4-Fluoro-phenyl)-ethyl]-6,8-dimethoxy-3,4-dihydro-1H-isoquinolin-2-yl}-ethyl)-3-quinolin-4-yl-urea 1-{2-[1-(4-Fluoro-benzyl)-6,7-dimethoxy-3,4-dihydro-1H-isoquinolin-2-yl]-ethyl}-3-(2-methyl-quinolin-4-yl)-urea 1-{2-[1-(3,4-Dimethoxy-benzyl)-7,8-dimethoxy-1,3,4,5-tetrahydro-benzo[c]azepin-2-yl]-ethyl}-3-(2-methyl-quinolin-4-yl)-urea 1-(2-{1-[(E)-2-(2,4-Difluoro-phenyl)-vinyl]-6,7-dimethoxy-3,4-dihydro-1H-isoquinolin-2-yl}-ethyl)-3-(2-methyl-quinolin-4-yl)-urea 1-(2-{1-[(E)-2-(2,5-Difluoro-phenyl)-vinyl]-6,7-dimethoxy-3,4-dihydro-1H-isoquinolin-2-yl}-ethyl)-3-(2-methyl-quinolin-4-yl)-urea 1-(2-{1-[2-(2,3-Difluoro-phenyl)-ethyl]-6,7-dimethoxy-3,4 dihydro-1H-isoquinolin-2-yl}-ethyl)-3-(2-methyl-quinolin-4-yl)-urea 1-(2-{1-[2-(2,4-Difluoro-phenyl)-ethyl]-6,7-dimethoxy-3,4-dihydro-1H-isoquinolin-2-yl}-ethyl)-3-(2-methyl-quinolin-4-yl)-urea 1-(2-{1-[2-(2,5-Bis-trifluoromethyl-phenyl)-ethyl]-6,7-dimethoxy-3,4-dihydro-1H-isoquinolin-2-yl}-ethyl)-3-(2-methyl-quinolin-4-yl)-urea 1-(2-{1-[2-(2,5-Difluoro-phenyl)-ethyl]-6,7-dimethoxy-3,4-dihydro-1H-isoquinolin-2-yl}-ethyl)-3-(2-methyl-quinolin-4-yl)-urea 1-(2-{1-[2-(3,4-Difluoro-phenyl)-ethyl]-6,7-dimethoxy-3,4-dihydro-1H-isoquinolin-2-yl}-ethyl)-3-(2-methyl-quinolin-4-yl)-urea 1-(2-{1-[2-(3,4-Dimethoxy-phenyl)-ethyl]-6,7-dimethoxy-3,4-dihydro-1H-isoquinolin-2-yl}-ethyl)-3-(2-methyl-quinolin-4-yl)-urea 1-(2-{1-[2-(3,5-Bis-trifluoromethyl-phenyl)-ethyl]-6,7-dimethoxy-3,4-dihydro-1H-isoquinolin-2-yl}-ethyl)-3-(2-methyl-quinolin-4-yl)-urea 1-(2-{1-[2-(4-Fluoro-phenyl)-ethyl]-6,7-dimethoxy-3,4-dihydro-1H-isoquinolin-2-yl}-ethyl)-3-(2-methyl-quinolin-4-yl)-urea 1-(2-{6,7-Dimethoxy-1-[2-(2-methoxy-phenyl)-ethyl]-3,4-dihydro-1H-isoquinolin-2-yl}-ethyl)-3-(2-methyl-quinolin-4-yl)-urea 1-(2-{6,7-Dimethoxy-1-[2-(3-methoxy-phenyl)-ethyl]-3,4-dihydro-1H-isoquinolin-2-yl}-ethyl)-3-(2-methyl-quinolin-4-yl)-urea 1-(2-{6,7-Dimethoxy-1-[2-(4-methoxy-phenyl)-ethyl]-3,4-dihydro-1H-isoquinolin-2-yl}-ethyl)-3-(2-methyl-quinolin-4-yl)-urea 1-(2-{6,7-Dimethoxy-1-[2-(4-trifluoromethyl-phenyl)-ethyl]-3,4-dihydro-1H-isoquinolin-2-yl}-ethyl)-3-(2-methyl-quinolinyl)-urea 1-[2-(6,7-Dimethoxy-1-phenethyl-3,4-dihydro-1H-isoquinolin-2-yl)-ethyl]-3-(2-methyl-quinolin-4-yl)-urea 1-[2-(6,7-Dimethoxy-1-phenethyl-3,4-dihydro-1H-isoquinolin-2-yl)-ethyl]-3-pyridin-4-yl-urea 1-[2-(6,7-Dimethoxy-1-phenethyl-3,4-dihydro-1H-isoquinolin-2-yl)-ethyl]-3-quinolinyl-4-urea 1-[3-(6,7-Dimethoxy-1-phenethyl-3,4-dihydro-1H-isoquinolin-2-yl)-propyl]-3-(2-methyl-quinolin-4-yl)-urea 1-[3-(6,7-Dimethoxy-1-phenethyl-3,4-dihydro-1H-isoquinolin-2-yl)-propyl]-3-quinolin-4-yl-urea 1-[2-(1-Benzo[1,3]dioxol-5-ylmethyl-6,7-dimethoxy-3,4-dihydro-1H-isoquinolin-2-yl)-ethyl]-3-(2-methyl-quinolin-4-yl)-urea 1-[2-(1-Benzo[1,3]dioxol-5-ylmethyl-6,7-dimethoxy-3,4-dihydro-1H-isoquinolin-2-yl)-ethyl]-3-pyridin-4-yl-urea 1-[2-(1-Benzo[1,3]dioxol-5-ylmethyl-6,7-dimethoxy-3,4-dihydro-1H-isoquinolin-2-yl)-ethyl]-3-quinolin-4-yl-urea 1-[2-(1-Benzyl-3,4-dihydro-1H-isoquinolin-2-yl)-ethyl]-3-pyridin-4-yl-urea 1-[2-(1-Benzyl-3,4-dihydro-1H-isoquinolin-2-yl)-ethyl]-3-quinolin-4-yl-urea 1-[2-(1-Benzyl-6,7-dimethoxy-3,4-dihydro-1H-isoquinolin-2-yl)-ethyl]-3-(2-methyl -quinolin-4-yl)-urea 1-[2-(1-Benzyl-6,7-dimethoxy-3,4-dihydro-1H-isoquinolin-2-yl)-ethyl]-3-pyridin-4-yl-urea 1-[2-(1-Benzyl-6,7-dimethoxy-3,4-dihydro-1H-isoquinolin-2-yl)-ethyl]-3-quinolin-4-yl-urea 1-[2-(1-Benzyl-6-methoxy-3,4-dihydro-1H-isoquinolin-2-yl)-ethyl]-3-pyridin-4-yl -urea 1-[2-(1-Benzyl-6-methoxy-3,4-dihydro-1H-isoquinolin-2-yl)-ethyl]-3-quinolinyl-4-yl-urea 1-[2-(6,7-Dimethoxy-1-naphthalen-2-ylmethyl-3,4-dihydro-1H-isoquinolin-2-yl)-ethyl]-3-pyridin-4-yl-urea 1-[2-(6,7-Dimethoxy-1-naphthalen-2-ylmethyl-3,4-dihydro-1H-isoquinolin-2-yl)-ethyl]-3-quinolin-4-yl-urea 1-[2-(6,7-Dimethoxy-1-phenoxymethyl-3,4-dihydro-1H-isoquinolin-2-yl)-ethyl]-3-pyridin-4-yl-urea 1-[3-(1-Benzyl-6,7-dimethoxy-3,4-dihydro-1H-isoquinolin-2-yl)-propyl]-3-(2-methyl-quinolin-4-yl)-urea 1-[3-(1-Benzyl-6,7-dimethoxy-3,4-dihydro-1H-isoquinolin-2-yl)-propyl]-3-quinolin-4-yl-urea 1-{2-[1-(2,5-Dimethoxy-benzyl)-6,7-dimethoxy-3,4-dihydro-1H-isoquinolin-2-yl]-ethyl}-3-pyridin-4-yl-urea 1-{2-[1-(2,5-Dimethoxy-benzyl)-6,7-dimethoxy-3,4-dihydro-1H-isoquinolin-2-yl]-ethyl}-3-quinolin-4-yl-urea 1-{2-[1-(2,6-Dichloro-benzyl)-6,7-dimethoxy-3,4-dihydro-1H-isoquinolin-2-yl]-ethyl}-3-(2-methyl-quinolin-4-yl)-urea 1-{2-[1-(3,4-Difluoro-benzyl)-6,7-dimethoxy-3,4-dihydro-1H-isoquinolin-2-yl]-ethyl}-3-pyridin-4-yl-urea 1-{2-[1-(3,4-Difluoro-benzyl)-6,7-dimethoxy-3,4-dihydro-1H-isoquinolin-2-yl]-ethyl}-3-quinolin-4-yl-urea 1-{2-[1-(3,4-Dimethoxy-benzyl)-6,7,8-trimethoxy-3,4-dihydro-1H-isoquinolin-2-yl]-ethyl}-3-quinolin-4-yl-urea 1-{2-[1-(3,4-Dimethoxy-benzyl)-6,7-dimethoxy-3,4-dihydro-1H-isoquinolin-2-yl]-ethyl}-3-pyridin-4-yl-urea 1-{2-[1-(3,4-Dimethoxy-benzyl)-6,7-dimethoxy-3,4-dihydro-1H-isoquinolin-2-yl]-ethyl}-3-quinolin-4-yl-urea 1-{2-[1-(3,4-Dimethoxy-benzyl)-6,7-dimethoxy-3,4-dihydro-1H-isoquinolin-2-yl]-ethyl}-3-(5,6,7,8-tetrahydro-quinolin-4-yl)-urea 1-{2-[1-(3,4-Dimethoxy-benzyl)-6,8-dimethoxy-3,4-dihydro-1H-isoquinolin-2-yl]-ethyl}-3-(2-methyl-quinolin-4-yl)-urea 1-{2-[1-(3,4-Dimethoxy-benzyl)-6,8-dimethoxy-3,4-dihydro-1H-isoquinolin-2-yl)-ethyl}-3-pyridin-4-yl-urea 1-{2-[1-(3,4-Dimethoxy-benzyl)-6,8-dimethoxy-3,4-dihydro-1H-isoquinolin-2-yl]-ethyl}-3-quinolin-4-yl-urea 1-{2-[1-(3,4-Dimethoxy-benzyl)-6-methoxy-3,4-dihydro-1H-isoquinolin-2-yl]-ethyl}-3-pyridin-4-yl-urea 1-{2-[1-(3,4-Dimethoxy-benzyl)-6-methoxy-3,4-dihydro-1H-isoquinolin-2-yl]-ethyl}-3-quinolin-4-yl-urea 1-{2-[1-(3-Fluoro-4-methoxy-benzyl)-6,7-dimethoxy-3,4-dihydro-1H-isoquinolin-2-yl]-ethyl}-3-(2-methyl-quinolin-4-yl)-urea 1-{2-[1-(3-Fluoro-5-trifluoromethyl-benzyl)-6,7-dimethoxy-3,4-dihydro-1H-isoquinolin-2-yl]-ethyl}-3-methyl-quinolin-4-yl)-urea 1-{2-[1-(4-Chloro-benzyl)-6,7-dimethoxy-3,4-dihydro-1H-isoquinolin-2-yl]-ethyl}-3-pyridin-4-yl-urea 1-{2-[1-(4-Chloro-benzyl)-6,7-dimethoxy-3,4-dihydro-1H-isoquinolin-2-yl]-ethyl}-3-quinolin-4-yl-urea 1-{2-[1-(4-Fluoro-benzyl)-6,7-dimethoxy-3,4-dihydro-1H-isoquinolin-2-yl]-ethyl}-3-pyridin-4-yl-urea 1-{2-[1-(4-Fluoro-benzyl)-6,7-dimethoxy-3,4-dihydro-1H-isoquinolin-2-yl]-ethyl}-3-quinolin-4-yl-urea 1-{2-[6,7-Dimethoxy-1-(2,3,4-trimethoxy-benzyl)-3,4-dihydro-1H-isoquinolin-2-yl]-ethyl}-3-pyridin-4-yl-urea 1-{2-[6,7-Dimethoxy-1-(2,3,4-trimethoxy-benzyl)-3,4-dihydro-1H-isoquinolin-2-yl]-ethyl}-3-quinolinyl-4-yl-urea 1-{2-[6,7-Dimethoxy-1-(3,4,5-trimethoxy-benzyl)-3,4-dihydro-1H-isoquinolin-2-yl]-ethyl}-3-(2-methyl-quinolin-4-yl)-urea 1-{2-[6,7-Dimethoxy-1-(3,4,5-trimethoxy-benzyl)-3,4-dihydro-1H-isoquinolin-2-yl]-ethyl}-3-pyridin-4-yl-urea 1-{2-[6,7-Dimethoxy-1-(3,4,5-trimethoxy-benzyl)-3,4-dihydro-1H-isoquinolin-2-yl]-ethyl}-3-quinolin-4-yl-urea 1-{2-[6,7-Dimethoxy-1-(3-methoxy-benzyl)-3,4-dihydro-1H-isoquinolin-2-yl]-ethyl}-3-pyridin-yl-urea 1-{2-[6,7-Dimethoxy-1-(3-methoxy-benzyl)-3,4-dihydro-1H-isoquinolin-2-yl]-ethyl}-3-quinolin-4-yl-urea 1-{2-[6,7-Dimethoxy-1-(4-methoxy-benzyl)-3,4-dihydro-1H-isoquinolin-2-yl]-ethyl}-3-pyridin-4-yl-urea 1-{2-[6,7-Dimethoxy-1-(4-methoxy-benzyl)-3,4-dihydro-1H-isoquinolin-2-yl]-ethyl}-3-quinolin-4-yl-urea 1-{3-[1-(3,4-Difluoro-benzyl)-6,7-dimethoxy-3,4-dihydro-1H-isoquinolin-2-yl]-propyl}-3-quinolin-4-yl-urea 1-{3-[1-(3,4-Dimethoxy-benzyl)-6,7-dimethoxy-3,4-dihydro-1H-isoquinolin-2-yl]-propyl}-3-(2-methyl-quinolin-4-yl)-urea 1-{3-[1-(3,4-Dimethoxy-benzyl)-6,7-dimethoxy-3,4-dihydro-1H-isoquinolin-2-yl]-propyl}-3-quinolin-4-yl-urea 1-{3-[1-(3,4-Dimethoxy-benzyl)-6,8-dimethoxy-3,4-dihydro-1H-isoquinolin-2-yl]-propyl}-3-(2-methyl-quinolin-4-yl)-urea 1-{3-[1-(3,4-Dimethoxy-benzyl)-6,8-dimethoxy-3,4-dihydro-1H-isoquinolin-2-yl]-propyl}-3-quinolinyl-4-urea 1-{3-[1-(4-Fluoro-benzyl)-6,7-dimethoxy-3,4-dihydro-1H-isoquinolin-2-yl]-propyl}-3-quinolin-4-yl-urea 1-{2-[5-(3,4-Dimethoxy-benzyl)-7,8-dihydro-5H-[1,3]dioxolo[4,5-g]isoquinolin-6-yl]-ethyl}-3-pyridin-4-yl-urea 1-{2-[5-(3,4-Dimethoxy-benzyl)-7,8-dihydro-5H-[1,3]dioxolo[4,5-g]isoquinolin-6-yl]-ethyl}-3-quinolin-4-yl-urea 1-{2-[6-(3,4-Dimethoxy-benzyl)-2,3,8,9-tetrahydro-6H-[1,4]dioxino[2,3-g]isoquinolin-7-yl]-ethyl}-3-pyridin-4-yl-urea 1-{2-[6-(3,4-Dimethoxy-benzyl)-2,3,8,9-tetrahydro-6H-[1,4]dioxino[2,3-g]isoquinolin-7-yl]-ethyl}-3-quinolin-4-yl-urea 1-[2-(1-Benzhydryl-5,8-dimethoxy-3,4-dihydro-1H-isoquinolin-2-yl)-ethyl]-3-quinolin-4-yl-urea 1-[2-(1-Benzhydryl-6,7-dimethoxy-3,4-dihydro-1H-isoquinolin-2-yl)-ethyl]-3-pyridin-4-yl-urea 1-[2-(1-Benzhydryl-6,7-dimethoxy-3,4-dihydro-1H-isoquinolin-2-yl)-ethyl]-3-quinolin-4-yl-urea 1-[2-(1-Benzyl-5,8-dimethoxy-3,4-dihydro-1H-isoquinolin-2-yl)-ethyl]-3-pyridin-4-yl-urea 1-[2-(1-Benzyl-5,8-dimethoxy-3,4-dihydro-1H-isoquinolin-2-yl)-ethyl]-3-quinolin-4-yl-urea 1-{2-[1-(3,4-Dimethoxy-benzyl)-5,8-dimethoxy-3,4-dihydro-1H-isoquinolin-2-yl]-ethyl}-3-quinolin-4-yl-urea 1-{2-[1-(2,5-Dimethoxy-benzyl)-5,8-dimethoxy-3,4-dihydro-1H-isoquinolin-2-yl]-ethyl}-3-quinolin-4-yl-urea 1-{2-[6,7-Dimethoxy-1-(1-phenyl-propyl)-3,4-dihydro-1H-isoquinolin-2-yl]-ethyl}-3-pyridin-4-yl-urea 1-{2-[6,7-Dimethoxy-1-(1-phenyl-propyl)-3,4-dihydro-1H-isoquinolin-2-yl]-ethyl}-3-quinolin-4yl-urea 1-{2-[1-(3,4-Dimethoxy-benzyl)-6,7-dimethoxy-4,4-dimethyl-3,4-dihydro-1H-isoquinolin-2-yl]-ethyl}-3-quinolin-4-yl-urea 1-{2-[(R)-1-(3,4-Dimethoxy-benzyl)-6,7-dimethoxy-3,4-dihydro-1H-isoquinolin-2-yl]-ethyl}-3-(2-methyl-quinolin-4-yl)-urea 1-{2-[(R)-1-(3,4-Dimethoxy-benzyl)-6,7-dimethoxy-3,4-dihydro-1H-isoquinolin-2-yl]-ethyl}-3-quinolin-4-yl-urea 1-{2-[(R)-1-(4-Fluoro-benzyl)-6,7-dimethoxy-3,4-dihydro-1H-isoquinolin-2-yl]-ethyl}-3-(2-methyl-quinolin-4-yl)-urea 1-{2-[7-Benzyloxy-1-(3,4-dimethoxy-benzyl)-6-methoxy-3,4-dihydro-1H-isoquinolin-2-yl]-ethyl}-3-(2-methyl-quinolin-4-yl)-urea 1-{2-[1-(3,4-Dimethoxy-benzyl)-6-methoxy-3,4-dihydro-1H-isoquinolin-2-yl]-ethyl}-3-(2-methyl-quinolin-4-yl)-urea 1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid methylamide 1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid propylamide 1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid dimethylamide 1-{2-[1-(4-Fluoro-benzyl)-6,7-dimethoxy-3,4-dihydro-1H-isoquinolin-2-yl]-ethyl}-3-(7-methyl-[1,8]naphthyridin-4-yl)-urea 1-{2-[1-(4-Fluoro-benzyl)-6,7-dimethoxy-3,4-dihydro-1H-isoquinolin-2-yl]-ethyl}-3-(5,6,7,8-tetrahydro-quinolin-4-yl)-urea 1-[2-(Benzyl-methyl-amino)-pyridin-4-yl]-3-{2-[1-(4-fluoro-benzyl)-6,7-dimethoxy-3,4-dihydro-1H-isoquinolin-2-yl]-ethyl}-urea 1-[2-(Benzyl-methyl-amino)-6-methyl-pyridin-4-yl]-3-{2-[1-(4-fluoro-benzyl)-6,7-dimethoxy-3,4-dihydro-1H-isoquinolin-2-yl]-ethyl}-urea 1-{2-[1-(4-Fluoro-benzyl)-6,7-dimethoxy-3,4-dihydro-1H-isoquinolin-2-yl]-ethyl}-3-[2-(methyl-phenyl-amino)-pyridin-4-yl]-urea 1-{2-[1-(4-Fluoro-benzyl)-6,7-dimethoxy-3,4-dihydro-1H-isoquinolin-2-yl]-ethyl}-3-(2-pyrrolidin-1-yl-pyridin-4-yl)-urea 1-{2-[1-(4-Fluoro-benzyl)-6,7-dimethoxy-3,4-dihydro-1H-isoquinolin-2-yl]-ethyl}-3-(2-methylamino-1-yl-pyridin-4-yl)-urea Quinolin-4-yl-carbamic acid 2-(6,7-dimethoxy-1-phenethyl-3,4-dihydro-1H-isoquinolin-2-yl)-ethyl ester Quinolin-4-yl-carbamic acid 2-(1-benzyl-6,7-dimethoxy-3,4-dihydro-1H-isoquinolin-2-yl)-ethyl ester Quinolin-4-yl-carbamic acid 2-[1-(4-fluoro-benzyl)-6,7-dimethoxy-3,4-dihydro-1H-isoquinolin-2-yl]-ethyl ester Quinolin-4-yl-carbamic acid 3-(1-benzyl-6,7-dimethoxy-3,4-dihydro-1H-isoquinolin-2-yl)-propyl ester Quinolin-4-yl-carbamic acid 3-(6,7-dimethoxy-1-phenethyl-3,4-dihydro-1H-isoquinolin-2-yl)-propyl ester Quinolin-4-yl-carbamic acid 3-[1-(3,4-difluoro-benzyl)-6,7-dimethoxy-3,4-dihydro-1H-isoquinolin-2-yl]-propyl ester Quinolin-4-yl-carbamic acid 3-[1-(3,4-dimethoxy-benzyl)-6,8-dimethoxy-3,4-dihydro-1H-isoquinolin-2-yl]-propyl ester Quinolin-4-yl-carbamic acid 3-[1-(4-fluoro-benzyl)-6,7-dimethoxy-3,4-dihydro-1H-isoquinolin-2-yl]-propyl ester Because of their ability to inhibit the actions of urotensin II, the described compounds can be used for treatment of diseases which are associated with an increase in vasoconstriction, proliferation or other disease states associated with the actions of urotensin II. Examples of such diseases are hypertension, atherosclerosis, angina or myocardial ischemia, congestive heart failure, cardiac insufficiency, cardiac arrhythmias, renal ischemia, chronic kidney disease, renal failure, stroke, cerebral vasospasm, cerebral ischemia, dementia, migraine, subarachnoidal hemorrhage, diabetes, diabetic arteriopathy, asthma, chronic obstructive pulmonary disease, high-altitude pulmonary edema, Raynaud's syndrome, portal hypertension, thyroid dysfunction, pulmonary edema, pulmonary hypertension, or pulmonary fibrosis. They can also be used for prevention of restenosis after balloon or stent angioplasty, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, addictions, schizophrenia, Alzheimer's disease, anxiety, obsessive-compulsive behavior, epileptic seizures, stress, depression, dementias, neuromuscular disorders, neurodegenerative diseases, as well as other diseases related to a dysregulation of urotensin II or urotensin II receptors.

These compositions may be administered in enteral or oral form e.g. as tablets, dragees, gelatine capsules, emulsions, solutions or suspensions, in nasal form like sprays or rectally in form of suppositories. These compounds may also be administered in intramuscular, parenteral or intravenous form, e.g. in form of injectable solutions.

These pharmaceutical compositions may contain the compounds of formula 1 as well as their pharmaceutically acceptable salts in combination with inorganic and/or organic excipients, which are usual in the pharmaceutical industry, like lactose, maize or derivatives thereof, talcum, stearic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti-oxidants etc.

The compounds of general formula 1 may also be used in combination with one or more other therapeutically useful substances e.g. α- and β-blockers like phentolamine, phenoxybenzamine, atenolol, propranolol, Uimolol, metoprolol, carteolol, carvedilol, etc.; with vasodilators like hydralazine, minoxidil, diazoxide, flosequinan, etc.; with calcium-antagonists like diltiazem, nicardipine, nimodipine, verapamil, nifedipine, etc.; with angiotensin converting enzyme-inhibitors like cilazapril, captopril, enalapril, lisinopril etc.; with potassium channel activators like pinacidil, chromakalim, etc.; with angiotensin receptor antagonists like losartan, valsartan, candesartan, irbesartan, eprosartan, telmisartan, and tasosartan, etc.; with diuretics like hydrochlorothiazide, chlorothiazide, acetolamide, bumetamide, furosemide, metolazone, chlortalidone, etc.; with sympatholytics like methyldopa, clonidine, guanabenz, reserpine, etc.; with endothelin receptor antagonists like bosentan, tezosentan, darusentan, atrasentan, enrasentan, or sitaxsentan, etc.; with anti-hyperlipidemic agents like lovastatin, pravistatin, fluvastatin, atorvastatin, cerivastatin, simvastatin, etc.; and other therapeutics which serve to treat high blood pressure, vascular disease or other disorders listed above.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses of equal weight per day. As usual children should receive lower doses which are adapted to body weight and age.

Compounds of the general formula 1 can be prepared using methods generally known in the art, according to the general sequence of reactions outlined below. For simplicity and clarity reasons sometimes only a few of the possible synthetic routes that lead to compounds of general formula 1 are described.

For the synthesis of compounds of general formula 1 general synthetic routes illustrated in Schemes A through E can be employed. In some instances one or another of the various groups ($R^1$ to $R^9$, X, Y, Z, n) might be incompatible with the assembly illustrated in Schemes A through E and so will require the use of protecting groups. The use of protecting groups is well known in the art (see for example "Protective Groups in Organic Synthesis, T. W. Greene, Wiley-Interscience, 1981). Particular groups that may require protection are amines (protected as amides or carbamates), alcohols (protected as esters or ethers) and carboxylic acids (protected as esters). For the purposes of this discussion, it will be assumed that such protecting groups as are necessary are in place.

1,2,3,4-Tetrahydroisoquinolines and 1,2,3,4-tetrahydrobenz[c]azepines of general structure I in Schemes A through C are either commercially available or are prepared in racemic or optically active form by methods well known in the art. For instance they can be prepared by a ring-closing condensation reaction of amides derived from the corresponding phenylethylamines or phenylpropylamines and the appropriate carboxylic acid under the action of $POCl_3$ or $PCl_5$, followed by treatment with a reducing agent such as $NaBH_4$ (Whaley W M, Govindachari T R "The preparation of 3,4-dihydroisoquinolines and related compounds by the Bischler-Napieralski reaction." Org. React. (1951) 6, 74–106. Finkelstein J, Chiang E, Brossi A "Synthesis of 1,2,3,4-tetrahydro-1,1,2,3,3,4,4,-heptamethyl-6,7-dimethoxyisoquinoline and related compounds as potential hypotensive agents." J. Med. Chem. (1971) 14, 584–588. Ukaji Z, Shimizu Y, Kenmoku Y, Ahmend A, Inomata K "Catalytic asymmetric addition of dialkylzinc to 3,4-dihydroisoquinoline N-oxides utilizing tartaric acid ester as a chiral auxiliary." Bull. Chem. Soc. Jpn. (2000), 73, 447–452. Zheng W, Nikulin V I, Konkar A A, Vansal S S, Shams G, Feller D R, Miller D D "2-Amino-4-benzyl-4,5,6,7-tetrahydrothiazolo[5,4-c]pyridines: novel selective beta3-adrenoceptor antagonists." J Med Chem (1999), 42, 2287–2294). Substantially enantiomerically pure 1-substituted-2-tetrahydroisoquinoline and I-substituted-2-tetrahydrobenzazepine derivatives are prepared by analogous methods (Polniaszek R. P. et al., J. Am. Chem. Soc. (1989) 111, 4859–4863). The key step of this asymmetric synthesis is a stereoselective hydride reduction of a chiral iminium ion obtained by Bischler-Napieralski reaction. For the preparation of (R)-1-substituted-2-tetrahydroisoquinoline derivatives the chirality resident in the substrate is derived from commercially available (R)-(+)-α-phenethylamine.

According to schemes A or B, appropriate 1,2,3,4-tetrahydroisoquinolines or 1,2,3,4-tetrahydrobenz[c]azepines of general structure I are N-alkylated with suitably protected aminoalkyl halides It or hydroxyalkyl halides III. Removal of the protecting group provides the amines IV or alcohols V. The intermediates IV and V are further elaborated to the final compounds of general formula 1 by stepwise treatment with a carbonylating agent such as carbonyldiimidazole, followed by reaction with a suitable amine VI in the presence of a strong base such as sodium hexamethyldisilazide. This provides the final compounds VII and VIII, which correspond to general formula 1, in which Y is NH or O, respectively, and in which n, X, Z and $R^1$ to $R^6$ have the definitions given in general formula 1.

SCHEME A:

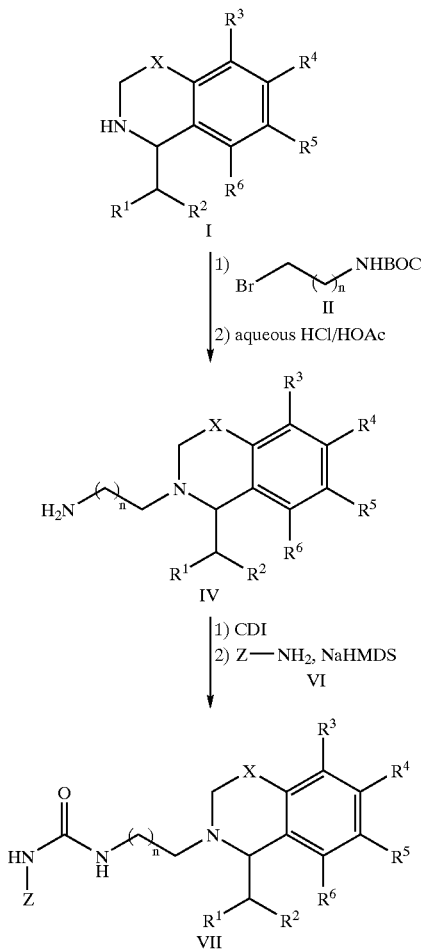

SCHEME B:

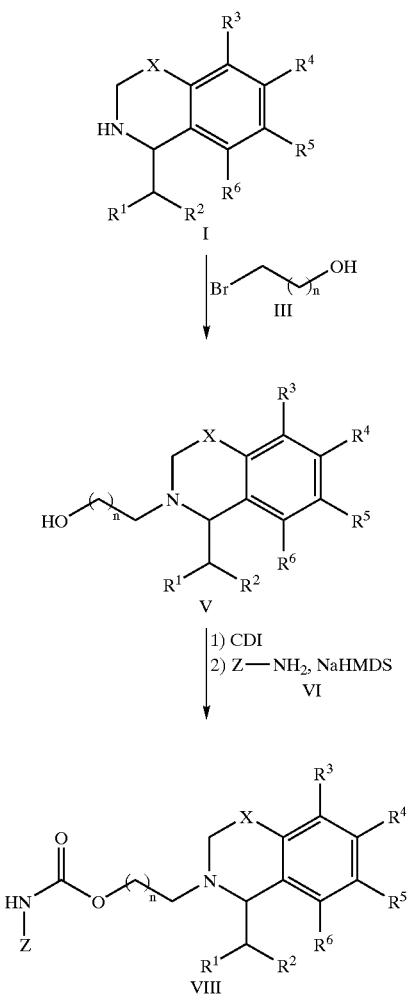

An alternative synthetic route to compounds of general formula 1 is illustrated in Scheme C. Thus, carboxylic acids of general structure IX are converted to their corresponding acyl azide, for example by the treatment with DPPA in a polar aprotic solvent such as DMF. The crude acyl azide is subjected to thermal rearrangement in an inert solvent such as toluene, to provide the corresponding isocyanate. Reaction of the crude isocyanate with alkyl amines of general structure IV or with alkyl alcohols of general structure V provides the target compounds VII or VII in which n, X, Y, Z and $R^1$ to $R^6$ have the definitions given in general formula 1.

An alternative synthetic route to compounds of general formula 1 is illustrated in Scheme D. Thus, 1,2,3,4-tetrahydroisoquinolines of general structure I are N-alkylated with compounds of general structure X (Russell RK et al. "Thiophene Systems. 9 Thienopyrimidinedione Derivatives as Potential Antihypertensive Agents" J Med Chem 1988, 31, 1786–1793) in an aprotic solvent such as THF in the presence of a scavenger base such as $NaHCO_3$ or di-isopropylethylamine, to provide the target compounds XI in which n, X, Y, Z and $R^1$ to $R^6$ have the definitions given in general formula 1.

Scheme D:

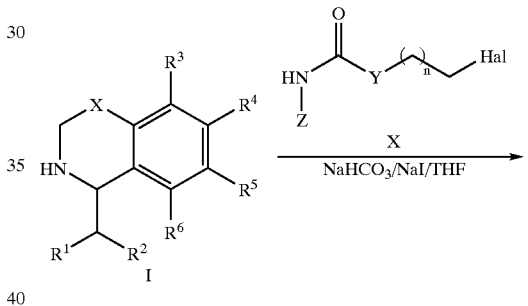

Scheme C:

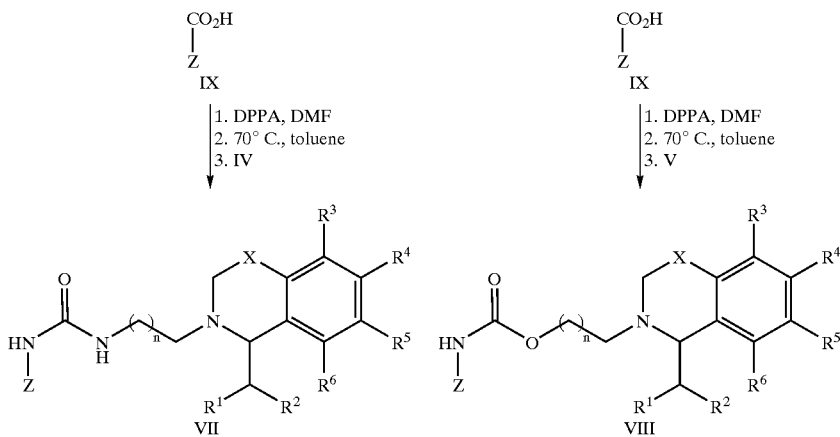

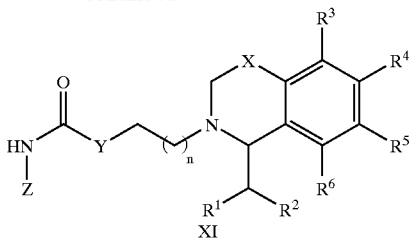

The preparation of the requisite intermediates of general structure X is illustrated in Scheme E, wherein Y, Z and n have the meaning given in general formula 1, and Hal stands for a halogen atom such as chloride. Commercially available or well-known heteroaryl amines of general structure VI are reacted with commercially available or well-known haloalkyl isocyanates, or haloalkyl chloroformates. Alternatively, compounds of general structure X are prepared by reaction of the isocyanate derived from heteroaryl carboxylic acids IX.

SCHEME E:

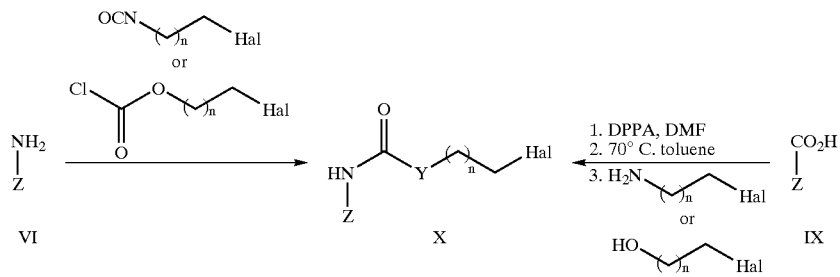

The foregoing general description of the Invention will now be further Illustrated by a number of examples which do not at all limit the scope of the invention.

EXAMPLES

List of Abbreviations

AcOH acetic acid
BSA bovine serum albumin
CDI carbonyldiimidazole
DIPEA diisopropylethylamine
DMAP 4-dimethylaminopyridine
DMF dimethylformamide
DMSO dimethylsulfoxide
DPPA diphenylphosphorylazide
EDC N-(3-dimethylaminopropyl)-N'-ethyl-carbodiimide
EDTA ethylenediamine tetra-acetic acid
EtOAc ethyl acetate
Et$_2$O diethyl ether
Hex hexane
HOBt 1-hydroxybenzotriazole
HPLC high performance liquid chromatography
HV high vacuum conditions
LC-MS liquid chromatography-mass spectroscopy
LAH lithium aluminum hydride
MeOH methanol
min minutes
MHz megahertz
NaHMDS sodium bis(trimethylsilyl)amide
NMR nuclear magnetic resonance
ppm part per million
PBS phosphate-buffered saline
PyBOP (benzotriazol-1-yloxy)-tripyrrolidinophosphonium hexafluorophosphate
rt room temperature
sat. saturated
TEA triethylamine
TFA trifluoroacetic acid
THF tetrahydrofuran
TLC thin layer chromatography
$t_R$ retention time Reactions are routinely performed under an inert atmosphere such as N$_2$ gas in air dried glassware. Solvents are used as received from the vendor. Evaporations are performed in a rotary evaporator at reduced pressure and a water bath temperature of 50° C. LCMS characterizations are performed on a Finnigan HP1100 platform using ESI ionization mode, and positive ion detection with a Navigator AQA detector. Analytical liquid chromatographic separations are performed on a C18 column of 4.6×30 mm dimensions and a mobile phase consisting of a 6 minute gradient of 2–95% CH$_3$CN in water containing 0.50% formic acid at a flow rate of 0.45 mL/min. Retention time ($t_R$) is given in min. TLC is performed on pre-coated silica gel 60 F$_{254}$ glass-backed plates (Merck). Preparative HPLC is performed on a Varian/Gilson platform using a C18 column of 21×60 mm dimensions and a mobile phase consisting of a gradient of 2–95% CH$_3$CN in water containing 0.5% formic acid.

Preparation of Intermediates

Example A

A1. (4-Fluoro-benzyl)-6,8-dimethoxy-1,2,3,4-tetrahydro-isoquinoline

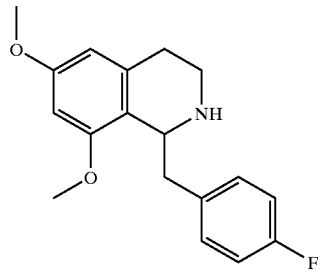

2-(3,5-Dimethoxy-phenyl)-ethylamine

To a suspension of LiAlH$_4$ (1.76 g, 46.4 mmol) in THF (30 mL) is added at 0° C. dropwise a solution of 1,3-dimethoxy-5-(2-nitro-vinyl)-benzene (2.43 g, 11.6 mmol; Gairaud C B, Lappin G R, J Org Chem 1953, 18, 1) in THF (70 mL). The mixture is stirred for 30 min at this temperature and then at reflux for 4 h. The reaction mixture is quenched by the subsequent addition of 2 N NaOH (20 mL) and stirred for another 15 min at ambient temperature. The aqueous solution is extracted three times with EtOAc. The combined organic layers are dried with anhydrous $MgSO_4$, filtered and concentrated to give the title compound as a yellow oil.

N-[2-(3,5-Dimethoxy-phenyl)-ethyl]-2-(4-fluoro-phenyl)-acetamide

To a solution of 2-(3,5-dimethoxy-phenyl)-ethylamine (1.01 g, 5.57 mmol) in anhydrous DMF (50 mL) is added 4-fluorophenyl acetic acid (860 mg, 5.57 mmol), PyBOP (3.17 g) and N-ethyldiisopropylamine (2.2 mL, 12.8 mmol). The mixture is stirred at rt for 14 h. Water (60 mL) is added, and the mixture is extracted with EtOAc (4×60 mL). The combined organic phases are washed with brine, dried over $MgSO_4$, filtered and concentrated in vacuo. The residue is purified by silica gel column chromatography (EtOAc/Hex, 7:3) to afford the title compound as a yellow oil.

1-(4-Fluoro-benzyl)-6,8-dimethoxy-1,2,3,4-tetrahydro-isoguinoline

To a stirred solution of N-[2-(3,5-dimethoxy-phenyl)-ethyl]-2–4-fluoro-phenyl)-acetamide (404 mg, 1.27 mmol) in $CH_3CN$ (3 mL) is added $POCl_3$ (350 μL, 3.82 mmol). The reaction mixture is stirred at reflux for 30 min. Concentration under reduced pressure gives a residual oil, which is dissolved in MeOH (10 mL). To this solution is added portionwise $NaBH_4$ (340 mg, 8.61 mmol) at 0° C. The reaction mixture is allowed to warm to rt and is stirred for 14 h. The reaction mixture is poured into water (15 mL) and extracted four times with $CH_2Cl_2$. The combined organic layers are dried over anhydrous $MgSO_4$, filtered and concentrated under reduced pressure. The residue is purified by flash column chromatography ($CH_2Cl_2$/MeOH, 9:1) to give the title compound as a brown oil.

Examples A2–A4

The following starting materials are prepared by the method of example A1:

A2. 1-(3,4-Dimethoxy-benzyl)-6,8-dimethoxy-1,2,3,4-tetrahydro-isoquinoline

A3. 1-(3,4-Difluoro-benzyl)-6,8-dimethoxy-1,2,3,4-tetrahydro-isoquinoline

A4. 1-(3-Fluoro-4-methoxy-benzyl)-6,8-dimethoxy-1,2,3,4-tetrahydro-isoquinoline

A5. 1-[2-(4-Fluoro-phenyl)-ethyl]-6,8-dimethoxy-1,2,3,4,-tetrahydro-isoguinoline

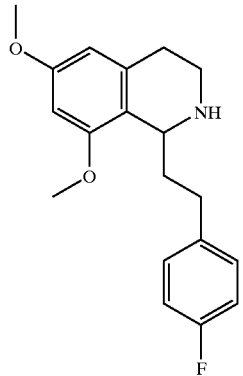

N-[2-(3,5-Dimethoxy-phenyl)-ethyl]-3-(4-fluoro-phenyl)-propionamide 2-(3,5-Dimethoxy-phenyl)ethylamine (1.20 g, 6.62 mmol) is dissolved in anhydrous DMF (50 mL), and 3-(4-fluorophenyl) propionic acid (1.113 g, 6.62 mmol), PyBOP (3.77 g) and DIPEA (2.61 mL, 15 mmol) are added. The mixture is stirred at rt for 14 h. Water (60 mL) is added, and the mixture is extracted with EtOAc (4×60 mL). The combined organic phases are washed with brine, dried over $MgSO_4$, filtered and concentrated in vacuo. The residue is purified by silica gel column chromatography (EtOAc/Hex, 7:3) to afford the title compound as a yellow oil.

1-[2-(4-Fluoro-phenyl)-ethyl]-6,8-dimethoxy-1,2,3,4,-tetrahydro-isoquinoline

To a stirred solution of N-[2-(3,5-dimethoxy-phenyl)-ethyl]-3-(4-fluoro-phenyl)-propionamide (1.25 g, 3.77 mmol) in $CH_3CN$ (12 mL) is added $POCl_3$ (1.04 mL, 11 mmol). The reaction mixture is stirred at reflux for 30 min. Concentration under reduced pressure gives a residual oil, which is dissolved in MeOH (35 mL). To this solution is added portionwise $NaBH_4$ (1.00 g, 26.4 mmol) at 0° C. and the reaction mixture is allowed to warm to rt and stir for 14 h. The mixture is poured into water (40 mL) and extracted with $CH_2Cl_2$ (4×40 mL). The combined organic layers are dried over anhydrous $MgSO_4$, filtered and concentrated under reduced pressure. The residue is purified by flash column chromatography ($CH_2Cl_2$/MeOH, 9:1) to give the title compound as a brown oil.

Examples A6–A7

The following starting materials are prepared according to the method of example A5:

A6. 1-[2-(2,4-Difluoro-phenyl)-ethyl]-6,8-dimethoxy-1,2,3,4-tetrahydro-isoquinoline A7. 1-[2-(3,4-Difluoro-phenylyethyl]-6,8-dimethoxy-1,2,3,4-tetrahydro-isoquinoline A8. 6,7-Dimethoxy-1-[2-(3-methoxy-phenyl)-ethyl]-1,2,3,4-tetrahydro-isoquinoline

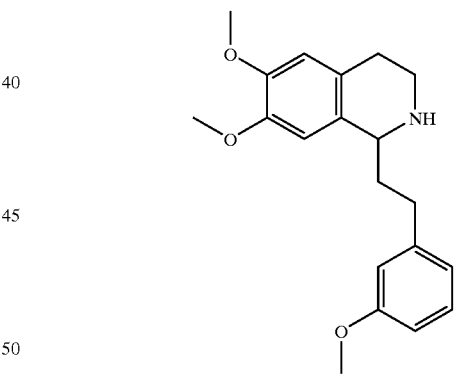

N-[2-(3,4-Dimethoxy-phenyl)-ethyl]-3-(3-methoxy-phenyl)-propionamide

To a suspension of 3-(3-methoxy-phenyl)-propionic acid (1.19 g, 6.62 mmol) and 3-dimethylamino-propyl)-ethyl-carbodiimide hydrochloride (1.33 g, 6.95 mmol) in THF (20 mL) is added 2-(3,4-dimethoxy-phenyl)-ethylamine (1.20 g, 6.62 mmol). The mixture is stirred at rt for 14 h. The mixture is poured onto $H_2O$ (100 mL) and EtOAc (100 mL). The organic layer is washed successively with saturated sodium hydrogen carbonate solution, 10% citric acid and saturated sodium chloride solution. The resulting organic layer is concentrated under reduced pressure to give the title compound.

6,7-Dimethoxy-1-[2-(3-methoxy-phenyl)-ethyl]-1,2,3,4-tetrahydro-isoquinoline

To a solution of N-[2-(3,4-dimethoxy-phenyl)-ethyl]-3–3-methoxy-phenyl)-propion-amide (2.21 g, 6.44 mmol) in THF (50 mL) is added POCl$_3$ (4.91 g, 32.2 mmol) and the resulting solution is refluxed for 1 h. After cooling to rt the solvent is removed under reduced pressure. The resulting oil is treated with methanol (20 mL) and evaporated again. The residue is dissolved in absolute methanol (40 mL) cooled to 0° C. and NaBH4 (1.21 g, 32.0 mmol) is added in portions. The resulting mixture is stirred at rt for 16 h, and then evaporated. To this residue is added water (150 mL). The aqueous layer is extracted with CH$_2$Cl$_2$ (3×50 mL). The combined extracts are dried over MgSO$_4$ and concentrated to give the title compound.

Examples A9–A45

The following starting materials are prepared according to the method of example A8:

A9. 1-[(E)-2-(2,3-Difluoro-phenyl)-vinyl]-6,7-dimethoxy-1,2,3,4-tetrahydro-isoquinoline A10. 1-[(E)-2-(2,4-Difluoro-phenyl)-vinyl]-6,7-dimethoxy-1,2,3,4-tetrahydro-isoquinoline A11. 1-[(E)-2-(2,5-Difluoro-phenyl)-vinyl]-6,7-dimethoxy-1,2,3,4-tetrahydro-isoquinoline A12. 1-[2-(2,5-Bis-trifluoromethyl-phenyl)-ethyl]-6,7-dimethoxy-1,2,3,4-tetrahydro-isoquinoline A13. 1-[2-(2,5-Difluoro-phenylyethyl]-6,7-dimethoxy-1,2,3,4-tetrahydro-isoquinoline A14. 1-[2–3,4-Difluoro-phenyl)-ethyl]-6,7-dimethoxy-1,2,3,4-tetrahydro-isoquinoline A15. 1-[2–3,4-Dimethoxy-phenyl)-ethyl]-6,7-dimethoxy-1,2,3,4-tetrahydro-isoquinoline A16. 1-[2-(3,5-Bis-trifluoromethyl-phenyl)-ethyl]-6,7-dimethoxy-1,2,3,4-tetrahydro-isoquinoline A17. 1-[2-(4-Fluoro-phenyl)-ethyl]-6,7-dimethoxy-1,2,3,4-tetrahydro-isoquinoline A18. 6,7-Dimethoxy-1-[2-(2-methoxy-phenyl)-ethyl]-1,2,3,4-tetrahydro-isoquinoline A19. 6,7-Dimethoxy-1-[2-(4-methoxy-phenyl)-ethyl]-1,2,3,4-tetrahydro-isoquinoline A20. 6,7-Dimethoxy-1-[2-(4-trifluoromethyl-phenyl)-ethyl]-1,2,3,4-tetrahydro-isoquinoline A21. 6,7-Dimethoxy-1-phenethyl-1,2,3,4-tetrahydro-isoquinoline A22. 1-(2,5-Dimethoxy-benzyl)-6,7-dimethoxy-1,2,3,4-tetrahydro-isoquinoline A23. 1-(2,6-Dichloro-benzyl)-6,7-dimethoxy-1,2,3,4-tetrahydro-isoquinoline A24. 1-(3,4-Difluoro-benzyl)-6,7-dimethoxy-1,2,3,4-tetrahydro-isoquinoline A25. 1-(3,4-Dimethoxy-benzyl)-6,7,8-trimethoxy-1,2,3,4-tetrahydro-isoquinoline A26. 1-(3,4-Dimethoxy-benzyl)-6,7-dimethoxy-1,2,3,4-tetrahydro-isoquinoline A27. 1-(3,4-Dimethoxy-benzyl)-6,7-dimethoxy-4,4-dimethyl-1,2,3,4-tetrahydro-isoquinoline A28. 1-(3-Fluoro-4-methoxy-benzyl)-6,7-dimethoxy-1,2,3,4-tetrahydro-isoquinoline A29. 1-(3-Fluoro-5-trifluoromethyl-benzyl)-6,7-dimethoxy-1,2,3,4-tetrahydro-isoquinoline A30. 1-(4-Chloro-benzyl)-6,7-dimethoxy-1,2,3,4-tetrahydro-isoquinoline A31. 1-(4-Fluoro-benzyl)-6,7-dimethoxy-1,2,3,4-tetrahydro-isoquinoline A32. 1-Benzhydryl-6,7-dimethoxy-1,2,3,4-tetrahydro-isoquinoline A33. 1-Benzo[1,3]dioxol-5-ylmethyl-6,7-dimethoxy-1,2,3,4-tetrahydro-isoquinoline A34. 1-Benzyl-6,7-dimethoxy-1,2,3,4-tetrahydro-isoquinoline A35. 6-(3,4-Dimethoxy-benzyl)-2,3,6,7,8,9-hexahydro-[1,4]dioxino[2,3-g]-isoquinoline A36. 6,7-Dimethoxy-1-(1-phenyl-propyl)-1,2,3,4-tetrahydro-isoquinoline A37. 6,7-Dimethoxy-1,2,3,4-trimethoxy-benzyl)-1,2,3,4-tetrahydro-isoquinoline A38. 6,7-Dimethoxy-1-(3,4,5-trimethoxy-benzyl)-1,2,3,4-tetrahydro-isoquinoline A39. 6,7-Dimethoxy-1-(3-methoxy-benzyl)-1,2,3,4-tetrahydro-isoquinoline A40. 6,7-Dimethoxy-1-(4-methoxy-benzyl)-1,2,3,4-tetrahydro-isoquinoline A41. 6,7-Dimethoxy-1-naphthalen-2-ylmethyl-1,2,3,4-tetrahydro-isoquinoline A42. 6,7-Dimethoxy-1-phenoxymethyl-1,2,3,4-tetrahydro-isoquinoline A43. 7-Benzyloxy-1-(3,4-dimethoxy-benzyl)-6-methoxy-1,2,3,4-tetrahydro-isoquinoline A44. 1-(3,4-Dimethoxy-benzyl)-6-methoxy-1,2,3,4-tetrahydro-isoquinoline A45. 1-(3,4-Dimethoxy-benzyl)-7,8-dimethoxy-2,3,4,5-tetrahydro-1H-benzo[c]azepine

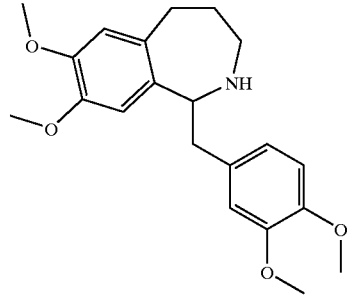

3-(3,4-Dimethoxy-phenyl)-propionamide

To a stirred solution of 3-(3,4-dimethoxy-phenyl)-propionic acid (10.0 g, 47.6 mmol) in dry THF (175 mL), under nitrogen, is added TEA (7.3 ml, 52.4 mmol). The resulting mixture is cooled to −10° C. before ethyl chloroformate (5.0 ml, 52 mmol) is added dropwise. After stirring at −10° C. (20 min), ammonium hydroxide (25% in water, 105 ml) in THF (105 mL) is added and the mixture is stirred at −15° C. for 30 min and then at rt for 1.5 h. The reaction mixture is concentrated in vacuo, extracted three times with CH$_2$Cl$_2$ and the combined organic extracts are washed with saturated aqueous NaHCO$_3$ and brine. The organic phase is dried over anhydrous MgSO$_4$, filtered and concentrated to give the title compound as a colorless solid.

3-(3,4-Dimethoxy-phenyl)-propylamine

A solution of 3-(3,4-dimethoxy-phenyl)-propionamide (11.1 g, 53.0 mmol) in anhydrous THF (400 ml) is slowly added to a stirred, ice-cooled suspension of LiAlH$_4$ (4.02 g, 106 mmol) in anhydrous THF (170 mL). Upon completion of the addition, the mixture is stirred at reflux for 2 h. After cooling to 0° C., H$_2$O (5 mL) and NaOH 1N (5 mL) are added dropwise to decompose the excess of hydride. The suspension is filtered and evaporated. The residue is partitioned between H₂O (40 mL) and CH₂Cl₂ (100 mL). The organic layer is washed with saturated aqueous NaHCO₃ and brine, dried over anhydrous MgSO₄, and concentrated under reduced pressure to give the title compound as a yellow oil.

2-(3,4-Dimethoxy-phenyl)-N-[3-(3,4-dimethoxy-phenyldropyl]-acetamide

A solution of 3-(3,4-dimethoxy-phenyl)-propylamine (12.5 g, 64.1 mmol) and TEA (10 mL, 71.8 mmol) in anhydrous THF (70 mL) is cooled to 0° C. and (3,4-dimethoxy-phenyl)-acetyl chloride (13.8 g, 64.1 mmol) in THF (28 mL) is added dropwise. After stirring at rt for 13 h under nitrogen, a saturated aqueous NaHCO₃ solution is added and the reaction mixture is extracted three times with EtOAc. The organic phase is dried over anhydrous MgSO₄, filtered and the solvent evaporated. The residue is washed with toluene and dried to give the title as a beige solid.

1-(3,4-Dimethoxy-benzyl)-7,8-dimethoxy-2,3,4,5-tetrahydro-1H-benzo[c]azepine

A mixture of 2-(3,4-dimethoxy-phenyl)-N-[3-(3,4-dimethoxy-phenyl)-propyl]-acetamide (6.16 g, 16.5 mmol) and POCl₃ (4.95 mL, 54.1 mmol) in anhydrous acetonitrile (185 mL) is stirred at reflux for 4 h under nitrogen. After cooling, the reaction mixture is evaporated and the residue is dissolved in MeOH (125 mL). The solution is cooled to 0° C. and NaBH₄ (4.31 g, 114 mmol) is added portionwise. After stirring at 0° C. for 2 h under nitrogen, the reaction mixture is poured into H₂O and extracted three times with CH₂Cl₂. The combined organic extracts are washed with brine, dried over anhydrous MgSO₄, filtered and concentrated to give a crude oil. Flash chromatography (CH₂Cl₂/MeOH: 9/1) yields the title compound as a yellow oil.

A46. 1-[2-(2,3-Difluoro-phenyl)-ethyl]-6,7-dimethoxy-1,2,3,4-tetrahydro-isoguinoline

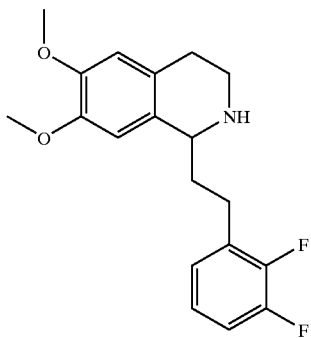

3-(2,3-Difluoro-phenyl)-propionic Acid

To a suspension of 2,3-difluoro-cinnamic acid (2.94 g, 16 mmol) in ethanol (100 mL) is added Pd (10% on carbon, 50 mg) and the mixture is treated with hydrogen (7.5 bar) for 15 h. The suspension is filtered through celite and the solvent evaporated to provide the title compound.

1-[2-(2,3-Difluoro-phenyl)-ethyl]-6,7-dimethoxy-1,2,3,4-tetrahydro-isoquinoline

The compound is prepared from 3-(2,3-difluoro-phenyl)-propionic acid and 2-(3,4-dimethoxy-phenyl)-ethylamine according to the method of example A8.

Example A47

The following starting material is prepared according to the method of example A46:

A47. 1-[2-(2,4-Difluoro-phenyl)-ethyl]-6,7-dimethoxy-1,2,3,4-tetrahydro-isoquinoline A48. 1-(3,4-Dichloro-benzyl)-6-methoxy-1,2,3,4-tetrahydro-isoguinoline-7-carboxylic acid dime thylamide.

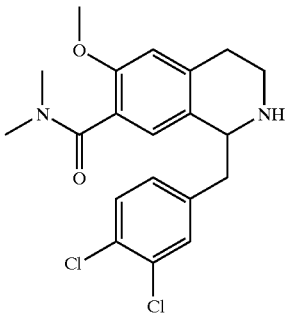

2-(4-Benzyloxy-3-methoxy-phenyl)-vinylamine

A stirred suspension of LAH (8.0 g, 0.21 mol) in THF (300 mL) is cooled in an ice bath and a solution of 4-benzyloxy-3-methoxynitrostyrene (15.0 g, 52.6 mmol) in THF (300 mL) is added dropwise. The green reaction mixture is allowed to warm to room temperature over 0.5 h, and is then refluxed for 4 h. The grey reaction mixture is treated successively with water (8 mL), 15% aqueous NaOH (8 mL), and water (24 mL). The resulting gray suspension is stirred at 50° C. for 20 min. The resulting yellow suspension is filtered, and the residue is washed with EtOAc. The combined filtrates are evaporated to provide the title compound as yellow oil which is used without further purification.

N-[2-(4-Benzyloxy-3-methoxy-phenyl)-vinyl]-2-(3,4-dichloro-phenyl)-acetamide

A mixture of 3,4-dichlorophenyl acetic acid (10.6 g, 51.7 mmol) and 2–4-benzyloxy-3-methoxy-phenyl)-vinylamine (12.1 g, 47 mmol) in toluene (100 mL) is heated at reflux in a Dean-Stark apparatus for 17 h. The reaction is allowed to cool to rt. Filtration yields the title compound as yellow crystals. The filtrate is heated again at reflux in a Dean-Stark apparatus for 16 h, and then allowed to cool to rt. Filtration provides a second portion of the title compound as yellow crystals. The two batches are combined and used without further purification.

7-Benzyloxy-1-(3,4-dichloro-benzyl)-6-methoxy-1,2,3,4-tetrahydro-isoquinoline

To a suspension of N-[2-(4-benzyloxy-3-methoxy-phenyl)-vinyl]-2-(3,4-dichloro-phenyl)-acetamide (13.3 g, 30 mmol) in CH₃CN (100 mL) at rt is added dropwise phosphoroxychloride (8.1 mL, 13.5 g, 88 mmol). The resulting white suspension is heated to reflux, and the resulting yellow solution is heated at reflux for 3 h. The dark yellow solution is allowed to cool and is evaporated to a yellow oil. The oil is taken up in MeOH (100 mL) and evaporated to yield an orange solid. The material is redissolved in MeOH (100 mL) and the solution is cooled to 0° C. NaBH₄ (3.61 g, 95 mmol) is added in portions with gas evolution and a strong exotherm. The resulting white suspension is stirred at rt for 16 h. The reaction mixture is partitioned between EtOAc (200 mL) and water (200 mL), and the aqueous phase is extracted with EtOAc (3×200 mL). The combined organic phase is washed with water and brine, and evaporated to provide the title compound as a faint yellow oil which is used without further purification.

1-(3,4-Dichloro-benzyl)-6-methoxy-1,2,3,4-tetrahydro-isoquinolin-7-ol

To a solution of 7-benzyloxy-1-(3,4-dichloro-benzyl)-6-methoxy-1,2,3,4-tetrahydro-isoquinoline (14.1 g, 30 mmol)

in MeOH (150 mL) and 1,2-dichlorobenzene (30 mL) is added 50% Pd on charcoal (500 mg). The reaction vessel is flushed with nitrogen and then with hydrogen at atmospheric pressure. After stirring at rt for 16 h, the reaction mixture is filtered through Hyflo, and evaporated to yield to the title compound as a beige solid which is used without further purification.

1-(3,4-Dichloro-benzyl)-7-hydroxy-6-methoxy-3,4-dihydro-1H-isoguinoline-2-carboxylic Acid Tert-butyl Ester To a solution of 1-(3,4-dichloro-benzyl)-6-methoxy-1,2,3,4-tetrahydro-isoquinolin-7-ol (9.6 g, 28 mmol) in isopropanol (30 mL) is added dropwise 1 M aqueous NaOH (30 mL) and di-tert-butyl-dicarbonate (6.7 g, 30.8 mmol). The resulting brown solution is stirred at rt for 30 min, and the resulting yellow solution is partioned between EtOAc (50 mL) and water (50 mL). The organic phase is washed successively with water and with brine, and is evaporated to provide the title compound as yellow oil, which is used without further purification.

1-(3,4-Dichloro-benzyl)-6-methoxy-7-trifluoromethanesulfonyloxy-3,4-dihydro-1H-isoquinoline-2-carboxylic Acid Tert-butyl Ester To a solution of 1-(3,4-dichloro-benzyl)-7-hydroxy-6-methoxy-3,4-dihydro-1H-isoquinoline-2-carboxylic acid tert-butyl ester (12 g, 27 mmol) in $CH_2Cl_2$ (100 mL) is added $Et_3N$ (3.8 mL, 27 mmol). The reaction mixture is cooled to 0° C. and trifluoromethanesulfonic anhydride (4.45 mL, 27 mmol) is added. The resulting yellow solution is stirred at rt 30 min, and is poured onto aqueous saturated $NaHCO_3$ (100 mL). The aqueous phase is extracted with $CH_2Cl_2$ (2×100 mL), and the combined organic phases are dried (MgSO4), filtered and evaporated to provide the title compound as yellow oil. Purification is achieved by crystallization from MeOH. The evaporated mother liquor furnishes additional material upon silica gel chromatography (heptane:Et2O, 9:1).

7-Cyano-1-(3,4-dichloro-benzyl)-6-methoxy-3,4-dihydro-1H-isoguinoline-2-carboxylic Acid Tert-butyl Ester A solution of 1-(3,4-dichloro-benzyl)-6-methoxy-7-trifluoromethanesulfonyloxy-3,4-dihydro-1H-isoquinoline-2-carboxylic acid tert-butyl ester (10 g, 17 mmol) in DMF (15 mL) standing over freshly dried 4 A molecular sieves is deoxygenated by bubbling with argon for 20 min. This solution is added to a deoxygenated suspension of zinc cyanide (4.6 g, 34 mmol) in DMF (15 mL) under argon. The resulting light brown suspension is placed in a 120° C. oil bath. Tetrakis-(triphenylphosphine)-palladium (1.0 g) is added, and the brown reaction mixture is stirred at 120° C. for 2 h. The reaction mixture is cooled to rt, and partitioned between EtOAc and saturated aqueous $NaHCO_3$. The mixture is filtered through Hyflo. The aqueous phase is extracted with EtOAc (3×40 mL). The combined organic phases are extracted with brine, dried over $MgSO_4$, filtered, and evaporated. The resulting yellow oil partially solidifies. The mixture is filtered and washed with $Et_2O$ to provide the title compound as white crystals. Evaporation of the filtrate and silica gel chromatography (EtOAc:heptane, 1:4) provides additional title compound as white crystals.

1-(3,4-Dichloro-benzyl)-6-methoxy-3,4-dihydro-1H-isoquinoline-2,7-dicarboxylic Acid 2-tert-butyl Ester To a solution of 7-cyano-1-(3,4-dichloro-benzyl)-6-methoxy-3,4-dihydro-1H-isoquinoline-2-carboxylic acid tert-butyl ester (3.60 g, 8.06 mmol) in benzyl alcohol (10 mL) is added KOH (3.00 g), and the reaction mixture is stirred at 160° C. for 0.5 h. The reaction mixture is allowed to cool to rt and is acidified with 2 M aqueous HCl. The reaction mixture is partitioned with EtOAc (3×20 mL). The combined organic phases are washed with brine, dried over $MgSO_4$, filtered, and evaporated to yield a yellow oil. Chromatography over silica gel with $CH_2Cl_2$:MeOH 19:1 and then with MeOH provides the title compound as yellow solid.

1-(3,4-Dichloro-benzyl)-7-dimethylcarbamoyl-6-methoxy-3,4-dihydro-1H-isoguinoline-2-carboxylic Acid Tert-butyl Ester To a solution of 1-(3,4-dichloro-benzyl)-6-methoxy-3,4-dihydro-1H-isoquinoline-2,7-dicarboxylic acid 2-tert-butyl ester (1.0 g, 2.1 mmol) in $CH_2Cl_2$ (10 mL) is added dimethylamine hydrochloride (0.35 g, 4.3 mmol), HOBt (65 mg, 0.43 mmo), DMAP (52 mg, 0.43 mmol), and EDC hydrochloride (493 mg, 2.6 mmol). The reaction mixture was stirred at rt for 16 h. The fine yellow suspension is diluted with $CH_2Cl_2$ (10 mL), and is washed with 1 M aqueous HCl and saturated aqueous $NaHCO_3$. The organic phase is dried over $MgSO_4$, filtered and evaporated to give the title compound.

1-(3,4-Dichloro-benzyl) 6-methoxy-1,2,3,4-tetrahydro-isoguinoline-7-carboxylic Acid Dimethylamide A solution of 1-(3,4-dichloro-benzyl)-7-dimethylcarbamoyl-6-methoxy-3,4-dihydro-1H-isoquinoline-2-carboxylic acid tert-butyl ester (1.0 g, 2.0 mmol) in 4 M HCl in dioxane is stirred at 0° C. for 1 h. The reaction mixture is evaporated to provide the title compound as a white solid.

Examples A49–A50

The following starting materials are prepared according to the method of example A48:

A49. 1-(3,4-Dichloro-benzyl)-6-methoxy-1,2,3,4-tetrahydro-isoquinoline-7-carboxylic acid methylamide A50. 1-(3,4-Dichloro-benzyl)-6-methoxy-1,2,3,4-tetrahydro-isoquinoline-7-carboxylic acid propylamide Examples A51–A52

Enantiomerically pure starting materials are prepared according to the method of Polniaszek R. P. et al., J. Am. Chem. Soc. (1989) 111, 4859–4863.

A51. (R)-1-(3,4-Dimethoxy-benzyl)-6,7-dimethoxy-1,2,3,4-tetrahydro-isoquinoline

A52. (R)-1-(4-Fluoro-benzyl)-6,7-dimethoxy-1,2,3,4-tetrahydro-isoquinoline

Preparation of Intermediates

Example B

B1. (2-Bromo-ethyl)-carbamic Acid Tert-butyl Ester

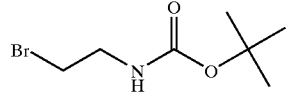

To 1 N aqueous NaOH (200 mL) is added to MeOH (400 mL) and the resulting solution is cooled to 20° C. 2-Bromoethylamine hydrobromide (25.0 g, 122 mmol) is added in a single portion, followed di-tert-butyl dicarbonate (26.6 g, 122 mmol). The reaction mixture is stirred for 2.5 h. The MeOH is removed on a rotary evaporator, and the aqueous suspension is extracted with $CH_2Cl_2$ (2×175 mL). The combined organic phases are extracted with 5% aqueous citric acid (300 mL), dried over $MgSO_4$, filtered, and evaporated to provide the title compound.

B2. (3-Chloro-propyl)-carbamic Acid Tert-butyl Ester

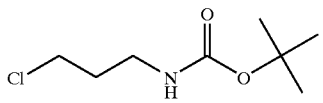

This material is prepared analogously to example B1 from 3-chloropropylamine.

Preparation of Intermediates

Example C

C1. 4-Amino-2-methylquinoline.

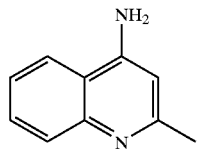

This material is commercially available.

C2. 4-Amino-pyridine.

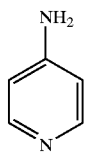

This material is commercially available.

C3. 4-Amino-quinoline.

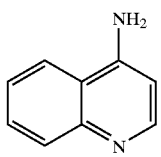

Prepared from commercial 4-nitroquinoline N-oxide according to the method described in Shinkai H et al., "4-Aminoquinolines: Novel Nociceptin Antagonists with Analgesic Activity", J. Med. Chem. (2000) 43, 4667–4677.

C4. 4-Amino-6,7,8,9-tetrahydro-quinoline.

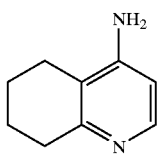

6,7,8,9-Tetrahydro-quinoline-N-oxide

A solution of 5,6,7,8-tetrahydroquinoline (2.66 mL, 20 mmol) in THF (125 mL) is cooled to 0° C. and a solution of m-chloroperbenzoic acid (3.8 g, 22 mmol) in THF (25 mL) is added. After 0.5 h the mixture is evaporated in vacuo and redissolved in $CH_2Cl_2$ (75 mL). The solution is washed with NaOH (1 M, 20 mL) and citric acid (10%, 20 mL), dried and evaporated to provide the title compound.

4-Nitro-6,7,8,9-tetrahydro-quinoline-N-oxide 5,6,7,8-Tetrahydroquinoline-N-oxide (298 mg, 2 mmol) is treated with a cooled mixture of $HNO_3$ (100%, 0.5 mL) and $H_2SO_4$ (98%, 0.7 mL). The mixture is heated to 80° C. for 2 h, poured into ice (100 g) and extracted with $CH_2Cl_2$ (30 mL). The organic phase is dreid and evaporated to provide the title compound.

4-Amino-6,7,8,9-tetrahydro-quinoline.

Prepared from 4-nitro-6,7,8,9-tetrahydro-quinoline-N-oxide according to the method of example C3.

C5. 4-Amino-7-methyl-[1,8]-naphthyridine.

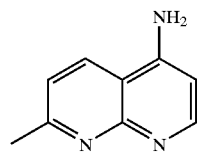

Prepared according to the method described in Barlin G B, Tan W L, "Potential Antimalarials. I 1,8-naphthyridines", Aust J Chem (1984) 37, 1065–1073. Radivov R, Haimova M, Simova E "Synthesis of 4-Amino-3-Pyridiyl and 4-Amino-5-Pyrimidyl Aryl Ketones and Related Compounds via an ortho-Lithiation Reaction", Synthesis (1986), 886–891.

C6. Quinoline-4-carboxylic Acid.

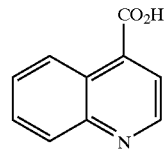

This material is commercially available.

C7. 2-Methyl-quinoline-4-carboxylic Acid.

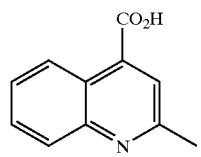

This material is prepared by reaction of isatin with acetone according to the method described in Brasyunas V B et al., "Synthesis of Quinoline-4-carboxylic acid and its derivatives", Chem. Heterocycl. Compd. (engi. Transl.) (1988) 670–673.

C8. 2-(Benzyl-methyl-amino)-isonicotinic Acid.

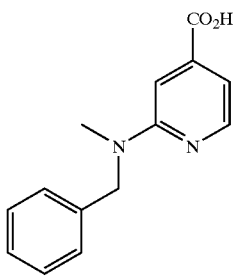

A mixture of 2-chloro-pyridine-4-carboxylic acid (300 mg, 1.9 mmol), benzylmethylamine (230 mg, 1.9 mmol) and triethylamine (192 mg, 1.9 mmol) is heated to 120° C. for 12 h. The residue is dissolved in $CH_2Cl_2$ (30 mL) and extracted with 1M NaOH (3×5 mL). The aqueous phase is adjusted to pH 2 and extracted with EtOAc (6×5 mL). The organic phases are combined, dried (MgSO₄), and evaporated to provide the title compound.

C9. 2-(Benzyl-methyl-amino)-6-methyl-isonicotinic Acid.

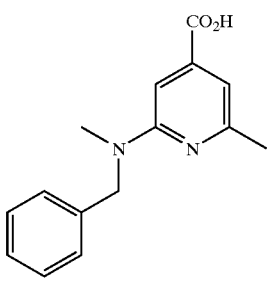

This material is prepared by reaction of 2-chloro-6-methyl-pyridine-4-carboxylic acid with benzylmethylamine analogously to example C8.

C10. 2-(Methyl-phenyl-amino)-isonicotinic Acid.

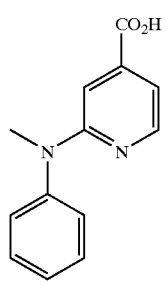

This material is prepared by reaction of 2-chloro-pyridine-4-carboxylic acid with N-methylaniline analogously to example C8.

C11. 2-Pyrrolidin-1-yl-isonicotinic Acid.

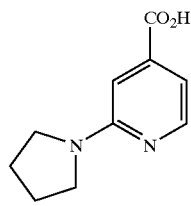

This material is prepared by reaction of 2-chloro-pyridine-4-carboxylic acid with pyrrolidine analogously to example C8.

Preparation of Intermediates

Example D

D1. 1-(2-Chloro-ethyl)-3-(2-methyl-quinolin-4-yl)-urea.

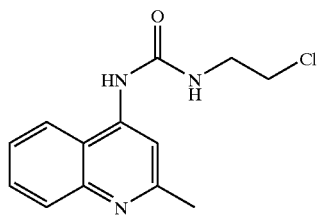

To a solution of 4-amino-2-methylquinoline (example C1, 12.6 g, 80 mmol) in THF (480 mL) is added 2-chloroethylisocyanate (10.2 mL, 120 mmol) at rt. The reaction mixture is stirred for 40 h at rt. MeOH (100 mL) is added, and stirring is continued an additional hour. The reaction mixture is evaporated and the residue is taken up in CH₂Cl₂. The organic phase is shaken with 1 N HCl (250 mL), and the resulting precipitate is collected by filtration. The solid is washed with CH₂Cl₂ (100 mL), saturated NaHCO₃ (2×100 mL), and with water (4×100 mL). The resulting solid is dried under HV at rt for 14 h to provide the title compound.

D2. 1-(3-Chloro-propyl)-3-(2-methyl-quinolin-4-yl)-urea.

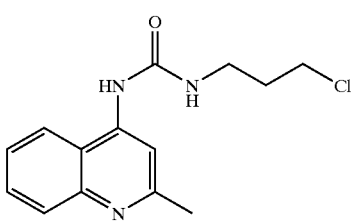

Analogously to method D1 the title compound is prepared from 4-amino-2-methylquinoline (example C1) and 3-chloropropylisocyanate.

D3. 1-(2-Chloro-ethyl)-3-(quinolin-4-yl)-urea.

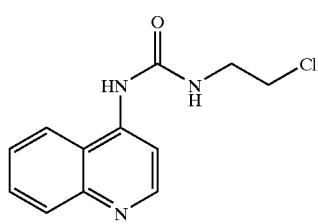

Analogously to method D1 the title compound is prepared from 4-amino-2-quinoline (example C3) and 2-chloroethylisocyanate.

D4. 1-(3-Chloro-propyl)-3-(quinolin-yl)-urea.

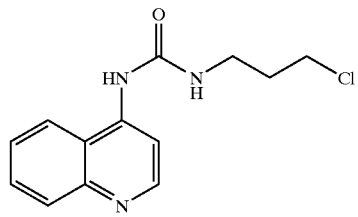

Analogously to method D1 the title compound is prepared from 4-amino-2-quinoline (example C3) and 3-chloropropylisocyanate.

D5. 1-(2-Chloro-ethyl)-3-(pyridin-4-yl)-urea.

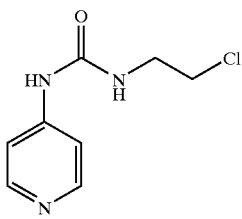

Analogously to method D1 the title compound is prepared from 4-amino-pyridine (example C2) and 2-chloroethylisocyanate.

D6. 1-(2-Chloro-ethyl)-3-(7-methyl-[1,8]-naphthyridin-4-yl)-urea.

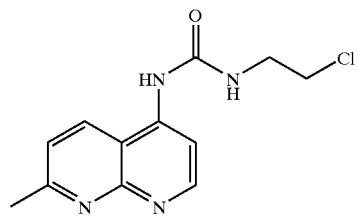

Analogously to method D1 the title compound is prepared from 4-amino-7-methyl-[1,8]-naphthyridine (example C5) and 2-chloroethylisocyanate.

Preparation of Final Products

Example 1
1-{2-[1-(4-Fluoro-benzyl)-6,8-dimethoxy-3,4-dihydro-1H-isoquinolin-2-yl]-ethyl}-3-(2-methyl-quinolin-4-yl)-urea.

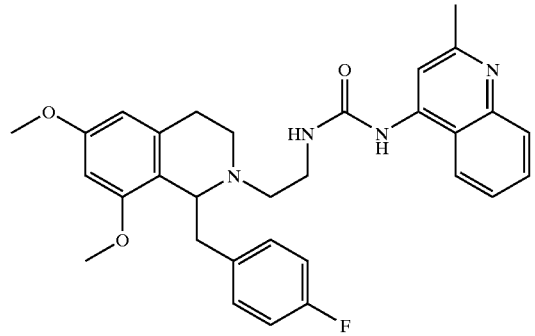

To a solution of 1-(4-fluoro-benzyl)-6,8-dimethoxy-1,2,3,4-tetrahydro-isoquinoline (example A1, 50 mg, 0.16 mmol) in anhydrous THF (2.5 mL) is added 1-(2-chloro-ethyl)-3-(2-methyl-quinolin-4-yl)-urea (example D1, 43.8 mg, 0.16 mmol), TEA (34.6 μL, 0.25 mmol) and NaI (2.5 mg, 0.017 mmol). The mixture is stirred at 75° C. for five days in a sealed flask. The reaction mixture is evaporated, and the residue is purified by preparative HPLC to provide the title compound.

LC-MS (MeCN/H$_2$O, 1:1) t$_R$=0.93 min, m/z=529.3 (M+1)

Examples 2–6

The additional examples set out in the following table are prepared starting from examples A1 to A4 and examples D1 or D3 using the method of example 1.

| Example No | Example | t$_R$ | [M + H]$^+$ |
|---|---|---|---|
| 2 | 1-{2-[1-(3,4-Difluoro-benzyl)-6,8-dimethoxy-3,4-dihydro-1H-isoquinolin-2-yl]-ethyl}-3-(2-methyl-quinolin-4-yl)-urea | 0.97 | 547.30 |
| 3 | 1-{2-[1-(3-Fluoro-4-methoxy-benzyl)-6,8-dimethoxy-3,4-dihydro-1H-isoquinolin-2-yl]-ethyl}-3-(2-methyl-quinolin-4-yl)-urea | 1.05 | 559.70 |
| 4 | 1-{2-[1-(3,4-Difluoro-benzyl)-6,8-dimethoxy-3,4-dihydro-1H-isoquinolin-2-yl]-ethyl}-3-quinolin-4-yl-urea | 0.80 | 533.30 |
| 5 | 1-{2-[1-(3-Fluoro-4-methoxy-benzyl)-6,8-dimethoxy-3,4-dihydro-1H-isoquinolin-2-yl]-ethyl}-3-quinolin-4-yl-urea | 1.13 | 545.24 |
| 6 | 1-{2-[1-(4-Fluoro-benzyl)-6,8-dimethoxy-3,4-dihydro-1H-isoquinolin-2-yl]-ethyl}-3-quinolin-4-yl-urea | 0.78 | 515.30 |

Example 7
1-{2-(4-Fluoro-phenyl)ethyl]-6,8-dimethoxy-3,4-dihydro-1H-isoquinolin-2-yl}-ethyl)-3-(2-methyl-quinoline-4-yl)-urea.

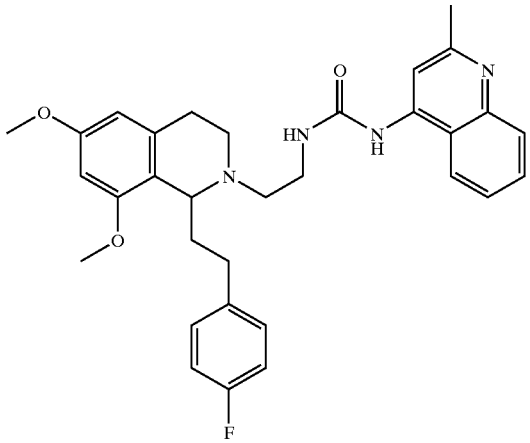

1-[2-(4-Fluoro-phenyl)-ethyl]-6,8-dimethoxy-1,2,3,4,-tetrahydro-isoquinoline (example A5, 100 mg, 0.317 mmol) is dissolved in anhydrous THF (3.0 mL), 1-(2-chloro-ethyl)-3-(2-methyl-quinolin-4-yl)-urea (example D1, 83.6 mg, 0.317 mmol), TEA (66.2 μL, 0.475 mmol) and NaI (4.8 mg, 0.032 mmol) are added. The mixture is stirred at 75° C. for five days in a sealed flask. The reaction mixture is evaporated, and the residue is purified by preparative HPLC to provide the title compound.

LC-MS (MeCN/H$_2$O, 1:1) $t_R$=1.11 min, m/z=543.5 (M+1)

Examples 8–9

The additional examples set out in the following table are prepared starting from examples A5 to A7 and examples D1 or D3 using the method of example 7.

| Example No | Example | $t_R$ | [M + H]$^+$ |
|---|---|---|---|
| 8 | 1-(2-{1-[2-(2,4-Difluoro-phenyl)-ethyl]-6,8-dimethoxy-3,4-dihydro-1H-isoquinolin-2-yl}-ethyl)-3-(2-methyl-quinolin-4-yl)-urea | 1.16 | 561.34 |
| 9 | 1-(2-{1-[2-(2,4-Difluoro-phenyl)-ethyl]-6,8-dimethoxy-3,4-dihydro-1H-isoquinolin-2-y}-ethyl)-3-quinolin-4-yl-urea | 1.15 | 547.32 |
| 10 | 1-(2-{1-[2-(3,4-Difluoro-phenyl)-ethyl]-6,8-dimethoxy-3,4-dihydro-1H-isoquinolin-2-yl}-ethyl)-3-(2-methyl-quinolin-4-yl)-urea | 1.16 | 561.33 |
| 11 | 1-(2-{1-[2-(3,4-Difluoro-phenyl)-ethyl]-6,8-dimethoxy-3,4-dihydro-1H-isoquinolin-2-yl}-ethyl)-3-quinolin-4-yl-urea | 1.16 | 547.31 |
| 12 | 1-(2-{1-[2-(4-Fluoro-phenyl)-ethyl]-6,8-dimethoxy-3,4-dihydro-1H-isoquinolin-2-yl}-ethyl)-3-quinolin-4-yl-urea | 1.15 | 529.30 |

Example 13
1-{2-[1-(4-Fluoro-benzyl)-6,7-dimethoxy-3,4-dihydro-1H-isoquinolin-2-yl]-ethyl}-3-(2-methyl-quinolin-4-yl)-urea.

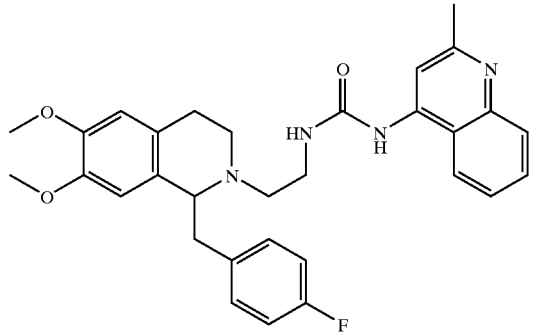

To a solution of 1-(4-fluorobenzyl)-6,7-dimethoxy-1,2,3,4-tetrahydro-isoquinoline (example A31, 0.16 g, 0.50 mmol) in THF (2 mL) is added 1-(2-chloroethyl)-3-(2-methylquinolin-yl)-urea (example D1, 0.18 g, 0.60 mmol), solid NaHCO$_3$ (50 mg, 0.6 mmol) and NaI (15 mg, 0.1 mmol). The mixture is stirred at 70° C. in a sealed flask for 5 days. The mixture is evaporated, and the residue is purified by preparative HPLC to provide the title compound.

LC-MS (MeCN/H$_2$O, 1:1) $t_R$=1.10 min, m/z=529.19 (M+1)

Examples 14–105

The additional examples set out in the following table are prepared starting from examples A1 to A52 and examples D1 to D5 using the method of example 13.

| Example No | Example | $t_R$ | [M + H]$^+$ |
|---|---|---|---|
| 14 | 1-{2-[1-(3,4-Dimethoxy-benzyl)-7,8-dimethoxy-1,3,4,5-tetrahydro-benzo[c]azepin-2-yl]-ethyl}-3-(2-methyl-quinolin-4-yl)-urea | 1.01 | 585.19 |
| 15 | 1-(2-{1-[(E)-2-(2,4-Difluoro-phenyl)-vinyl]-6,7-dimethoxy-3,4-dihydro-1H-isoquinolin-2-yl}-ethyl)-3-(2-methyl-quinolin-4-yl)-urea | 1.13 | 559.31 |
| 16 | 1-(2-{1-[(E)-2-(2,5-Difluoro-phenyl)-vinyl]-6,7-dimethoxy-3,4-dihydro-1H-isoquinolin-2-yl}-ethyl)-3-(2-methyl-quinolin-4-yl)-urea | 1.13 | 559.30 |
| 17 | 1-(2-{1-[2-(2,3-Difluoro-phenyl)-ethyl]-6,7-dimethoxy-3,4-dihydro-1H-isoquinolin-2-yl}-ethyl)-3-(2-methyl-quinolin-4-yl)-urea | 1.14 | 561.33 |
| 18 | 1-(2-{1-[2-(2,4-Difluoro-phenyl)-ethyl]-6,7-dimethoxy-3,4-dihydro-1H-isoquinolin-2-yl}-ethyl)-3-(2-methyl-quinolin-4-yl)-urea | 1.14 | 561.34 |
| 19 | 1-(2-{1-[2-(2,5-Bis-trifluoromethyl-phenyl)-ethyl]-6,7-dimethoxy-3,4-dihydro-1H-isoquinolin-2-yl}-ethyl)-3-(2-methyl-quinolin-4-yl)-urea | 1.18 | 661.30 |
| 20 | 1-(2-{1-[2-(2,5-Difluoro-phenyl)-ethyl]-6,7-dimethoxy-3,4-dihydro-1H-isoquinolin-2-yl}-ethyl)-3-(2-methyl-quinolin-4-yl)-urea | 1.14 | 561.32 |
| 21 | 1-(2-{1-[2-(3,4-Difluoro-phenyl)-ethyl]-6,7-dimethoxy-3,4-dihydro-1H-isoquinolin-2-yl}-ethyl)-3-(2-methyl-quinolin-4-yl)-urea | 1.14 | 561.32 |
| 22 | 1-(2-{1-[2-(3,4-Dimethoxy-phenyl)-ethyl]-6,7-dimethoxy-3,4-dihydro-1H-isoquinolin-2-yl}-ethyl)-3-(2-methyl-quinolin-4-yl)-urea | 1.09 | 585.37 |
| 23 | 1-(2-{1-[2-(3,5-Bis-trifluoromethyl-phenyl)-ethyl]-6,7-dimethoxy-3,4-dihydro-1H-isoquinolin-2-yl}-ethyl)-3-(2-methyl-quinolin-4-yl)-urea | 1.19 | 661.30 |
| 24 | 1-(2-{1-[2-(4-Fluoro-phenyl)-ethyl]-6,7-dimethoxy-3,4-dihydro-1H-isoquinolin-2-yl}-ethyl)-3-(2-methyl-quinolin-4-yl)-urea | 1.14 | 543.32 |

-continued

| Example No | Example | $t_R$ | $[M + H]^+$ |
|---|---|---|---|
| 25 | 1-(2-{6,7-Dimethoxy-1-[2-(2-methoxy-phenyl)-ethyl]-3,4-dihydro-1H-isoquinolin-2-yl}-ethyl)-3-(2-methyl-quinolin-4-yl)-urea | 1.13 | 555.36 |
| 26 | 1-(2-{6,7-Dimethoxy-1-[2-(3-methoxy-phenyl)-ethyl]-3,4-dihydro-1H-isoquinolin-2-yl}-ethyl)-3-(2-methyl-quinolin-4-yl)-urea | 1.13 | 555.36 |
| 27 | 1-(2-{6,7-Dimethoxy-1-[2-(4-methoxy-phenyl)-ethyl]-3,4-dihydro-1H-isoquinolin-2-yl}-ethyl)-3-(2-methyl-quinolin-4-yl)-urea | 1.13 | 555.37 |
| 28 | 1-(2-{6,7-Dimethoxy-1-[2-(4-trifluoromethyl-phenyl)-ethyl]-3,4-dihydro-1H-isoquinolin-2-yl}-ethyl)-3-(2-methyl-quinolin-4-yl)-urea | 1.17 | 593.35 |
| 29 | 1-[2-(6,7-Dimethoxy-1-phenethyl-3,4-dihydro-1H-isoquinolin-2-yl)-ethyl]-3-(2-methyl-quinolin-4-yl)-urea | 1.11 | 525.22 |
| 30 | 1-[2-(6,7-Dimethoxy-1-phenethyl-3,4-dihydro-1H-isoquinolin-2-yl)-ethyl]-3-pyridin-4-yl-urea | 1.07 | 461.12 |
| 31 | 1-[2-(6,7-Dimethoxy-1-phenethyl-3,4-dihydro-1H-isoquinolin-2-yl)-ethyl]-3-quinolin-4-yl-urea | 1.11 | 511.07 |
| 32 | 1-[3-(6,7-Dimethoxy-1-phenethyl-3,4-dihydro-1H-isoquinolin-2-yl)-propyl]-3-(2-methyl-quinolin-4-yl)-urea | 1.11 | 539.26 |
| 33 | 1-[3-(6,7-Dimethoxy-1-phenethyl-3,4-dihydro-1H-isoquinolin-2-yl)-propyl]-3-quinolin-4-yl-urea | 1.10 | 525.18 |
| 34 | 1-[2-(1-Benzo[1,3]dioxol-5-ylmethyl-6,7-dimethoxy-3,4-dihydro-1H-isoquinolin-2-yl)-ethyl]-3-(2-methyl-quinolin-4-yl)-urea | 1.14 | 555.21 |
| 35 | 1-[2-(1-Benzo[1,3]dioxol-5-ylmethyl-6,7-dimethoxy-3,4-dihydro-1H-isoquinolin-2-yl)-ethyl]-3-pyridin-4-yl-urea | 0.99 | 491.07 |
| 36 | 1-[2-(1-Benzo[1,3]dioxol-5-ylmethyl-6,7-dimethoxy-3,4-dihydro-1H-isoquinolin-2-yl)-ethyl]-3-quinolin-4-yl-urea | 1.06 | 541.07 |
| 37 | 1-[2-(1-Benzyl-3,4-dihydro-1H-isoquinolin-2-yl)-ethyl]-3-pyridin-4-yl-urea | 1.03 | 387.12 |
| 38 | 1-[2-(1-Benzyl-3,4-dihydro-1H-isoquinolin-2-yl)-ethyl]-3-quinolin-4-yl-urea | 1.10 | 437.08 |
| 39 | 1-[2-(1-Benzyl-6,7-dimethoxy-3,4-dihydro-1H-isoquinolin-2-yl)-ethyl]-3-(2-methyl-quinolin-4-yl)-urea | 1.09 | 511.17 |
| 40 | 1-[2-(1-Benzyl-6,7-dimethoxy-3,4-dihydro-1H-isoquinolin-2-yl)-ethyl]-3-pyridin-4-yl-urea | 0.98 | 447.10 |
| 41 | 1-[2-(1-Benzyl-6,7-dimethoxy-3,4-dihydro-1H-isoquinolin-2-yl)-ethyl]-3-quinolin-4-yl-urea | 1.07 | 497.08 |
| 42 | 1-[2-(1-Benzyl-6-methoxy-3,4-dihydro-1H-isoquinolin-2-yl)-ethyl]-3-pyridin-4-yl-urea | 1.06 | 417.09 |
| 43 | 1-[2-(1-Benzyl-6-methoxy-3,4-dihydro-1H-isoquinolin-2-yl)-ethyl]-3-quinolin-4-yl-urea | 1.11 | 467.12 |
| 44 | 1-[2-(6,7-Dimethoxy-1-naphthalen-2-ylmethyl-3,4-dihydro-1H-isoquinolin-2-yl)-ethyl]-3-pyridin-4-yl-urea | 1.10 | 497.10 |
| 45 | 1-[2-(6,7-Dimethoxy-1-naphthalen-2-ylmethyl-3,4-dihydro-1H-isoquinolin-2-yl)-ethyl]-3-quinolin-4-yl-urea | 1.12 | 547.14 |
| 46 | 1-[2-(6,7-Dimethoxy-1-phenoxymethyl-3,4-dihydro-1H-isoquinolin-2-yl)-ethyl]-3-pyridin-4-yl-urea | 0.98 | 463.09 |
| 47 | 1-[3-(1-Benzyl-6,7-dimethoxy-3,4-dihydro-1H-isoquinolin-2-yl)-propyl]-3-(2-methyl-quinolin-4-yl)-urea | 1.08 | 525.25 |
| 48 | 1-[3-(1-Benzyl-6,7-dimethoxy-3,4-dihydro-1H-isoquinolin-2-yl)-propyl]-3-quinolin-4-yl-urea | 1.04 | 511.17 |
| 49 | 1-{2-[1-(2,5-Dimethoxy-benzyl)-6,7-dimethoxy-3,4-dihydro-1H-isoquinolin-2-yl]-ethyl}-3-pyridin-4-yl-urea | 1.04 | 507.10 |
| 50 | 1-{2-[1-(2,5-Dimethoxy-benzyl)-6,7-dimethoxy-3,4-dihydro-1H-isoquinolin-2-yl]-ethyl}-3-quinolin-4-yl-urea | 1.10 | 557.11 |
| 51 | 1-{2-[1-(2,6-Dichloro-benzyl)-6,7-dimethoxy-3,4-dihydro-1H-isoquinolin-2-yl]-ethyl}-3-(2-methyl-quinolin-4-yl)-urea | 1.12 | 579.26 |
| 52 | 1-{2-[1-(3,4-Difluoro-benzyl)-6,7-dimethoxy-3,4-dihydro-1H-isoquinolin-2-yl]-ethyl}-3-pyridin-4-yl-urea | 1.04 | 483.10 |
| 53 | 1-{2-[1-(3,4-Difluoro-benzyl)-6,7-dimethoxy-3,4-dihydro-1H-isoquinolin-2-yl]-ethyl}-3-quinolin-4-yl-urea | 1.10 | 533.04 |

-continued

| Example No | Example | $t_R$ | $[M + H]^+$ |
|---|---|---|---|
| 54 | 1-{2-[1-(3,4-Dimethoxy-benzyl)-6,7,8-trimethoxy-3,4-dihydro-1H-isoquinolin-2-yl]-ethyl}-3-quinolin-4-yl-urea | 1.10 | 587.11 |
| 55 | 1-{2-[1-(3,4-Dimethoxy-benzyl)-6,7-dimethoxy-3,4-dihydro-1H-isoquinolin-2-yl]-ethyl}-3-pyridin-4-yl-urea | 0.94 | 507.16 |
| 56 | 1-{2-[1-(3,4-Dimethoxy-benzyl)-6,7-dimethoxy-3,4-dihydro-1H-isoquinolin-2-yl]-ethyl}-3-quinolin-4-yl-urea | 1.01 | 557.12 |
| 57 | 1-{2-[1-(3,4-Dimethoxy-benzyl)-6,7-dimethoxy-3,4-dihydro-1H-isoquinolin-2-yl]-ethyl}-3-(5,6,7,8-tetrahydro-quinolin-4-yl)-urea | 0.83 | 561.30 |
| 58 | 1-{2-[1-(3,4-Dimethoxy-benzyl)-6,8-dimethoxy-3,4-dihydro-1H-isoquinolin-2-yl]-ethyl}-3-(2-methyl-quinolin-4-yl)-urea | 1.11 | 571.21 |
| 59 | 1-{2-[1-(3,4-Dimethoxy-benzyl)-6,8-dimethoxy-3,4-dihydro-1H-isoquinolin-2-yl]-ethyl}-3-pyridin-4-yl-urea | 1.08 | 507.16 |
| 60 | 1-{2-[1-(3,4-Dimethoxy-benzyl)-6,8-dimethoxy-3,4-dihydro-1H-isoquinolin-2-yl]-ethyl}-3-quinolin-4-yl-urea | 1.11 | 557.18 |
| 61 | 1-{2-[1-(3,4-Dimethoxy-benzyl)-6-methoxy-3,4-dihydro-1H-isoquinolin-2-yl]-ethyl}-3-pyridin-4-yl-urea | 1.02 | 477.10 |
| 62 | 1-{2-[1-(3,4-Dimethoxy-benzyl)-6-methoxy-3,4-dihydro-1H-isoquinolin-2-yl]-ethyl}-3-quinolin-4-yl-urea | 1.08 | 527.10 |
| 63 | 1-{2-[1-(3-Fluoro-4-methoxy-benzyl)-6,7-dimethoxy-3,4-dihydro-1H-isoquinolin-2-yl]-ethyl}-3-(2-methyl-quinolin-4-yl)-urea | 1.11 | 559.33 |
| 64 | 1-{2-[1-(3-Fluoro-5-trifluoromethyl-benzyl)-6,7-dimethoxy-3,4-dihydro-1H-isoquinolin-2-yl]-ethyl}-3-(2-methyl-quinolin-4-yl)-urea | 1.15 | 597.33 |
| 65 | 1-{2-[1-(4-Chloro-benzyl)-6,7-dimethoxy-3,4-dihydro-1H-isoquinolin-2-yl]-ethyl}-3-pyridin-4-yl-urea | 1.09 | 481.04 |
| 66 | 1-{2-[1-(4-Chloro-benzyl)-6,7-dimethoxy-3,4-dihydro-1H-isoquinolin-2-yl]-ethyl}-3-quinolin-4-yl-urea | 1.11 | 531.08 |
| 67 | 1-{2-[1-(4-Fluoro-benzyl)-6,7-dimethoxy-3,4-dihydro-1H-isoquinolin-2-yl]-ethyl}-3-pyridin-4-yl-urea | 1.01 | 465.11 |
| 68 | 1-{2-[1-(4-Fluoro-benzyl)-6,7-dimethoxy-3,4-dihydro-1H-isoquinolin-2-yl]-ethyl}-3-quinolin-4-yl-urea | 1.09 | 515.06 |
| 69 | 1-{2-[6,7-Dimethoxy-1-(2,3,4-trimethoxy-benzyl)-3,4-dihydro-1H-isoquinolin-2-yl]-ethyl}-3-pyridin-4-yl-urea | 1.00 | 537.17 |
| 70 | 1-{2-[6,7-Dimethoxy-1-(2,3,4-trimethoxy-benzyl)-3,4-dihydro-1H-isoquinolin-2-yl]-ethyl}-3-quinolin-4-yl-urea | 1.08 | 587.09 |
| 71 | 1-{2-[6,7-Dimethoxy-1-(3,4,5-trimethoxy-benzyl)-3,4-dihydro-1H-isoquinolin-2-yl]-ethyl}-3-(2-methyl-quinolin-4-yl)-urea | 1.12 | 601.29 |
| 72 | 1-{2-[6,7-Dimethoxy-1-(3,4,5-trimethoxy-benzyl)-3,4-dihydro-1H-isoquinolin-2-yl]-ethyl}-3-pyridin-4-yl-urea | 0.96 | 537.09 |
| 73 | 1-{2-[6,7-Dimethoxy-1-(3,4,5-trimethoxy-benzyl)-3,4-dihydro-1H-isoquinolin-2-yl]-ethyl}-3-quinolin-4-yl-urea | 1.03 | 587.11 |
| 74 | 1-{2-[6,7-Dimethoxy-1-(3-methoxy-benzyl)-3,4-dihydro-1H-isoquinolin-2-yl]-ethyl}-3-pyridin-4-yl-urea | 1.00 | 477.11 |
| 75 | 1-{2-[6,7-Dimethoxy-1-(3-methoxy-benzyl)-3,4-dihydro-1H-isoquinolin-2-yl]-ethyl}-3-quinolin-4-yl-urea | 1.08 | 527.10 |
| 76 | 1-{2-[6,7-Dimethoxy-1-(4-methoxy-benzyl)-3,4-dihydro-1H-isoquinolin-2-yl]-ethyl}-3-pyridin-4-yl-urea | 0.99 | 477.12 |
| 77 | 1-{2-[6,7-Dimethoxy-1-(4-methoxy-benzyl)-3,4-dihydro-1H-isoquinolin-2-yl]-ethyl}-3-quinolin-4-yl-urea | 1.07 | 527.11 |
| 78 | 1-{3-[1-(3,4-Difluoro-benzyl)-6,7-dimethoxy-3,4-dihydro-1H-isoquinolin-2-yl]-propyl}-3-quinolin-4-yl-urea | 1.09 | 547.18 |
| 79 | 1-{3-[1-(3,4-Dimethoxy-benzyl)-6,7-dimethoxy-3,4-dihydro-1H-isoquinolin-2-yl]-propyl}-3-(2-methyl-quinolin-4-yl)-urea | 1.03 | 585.20 |

-continued

| Example No | Example | $t_R$ | $[M + H]^+$ |
|---|---|---|---|
| 80 | 1-{3-[1-(3,4-Dimethoxy-benzyl)-6,7-dimethoxy-3,4-dihydro-1H-isoquinolin-2-yl]-propyl}-3-quinolin-4-yl-urea | 1.01 | 571.19 |
| 81 | 1-{3-[1-(3,4-Dimethoxy-benzyl)-6,8-dimethoxy-3,4-dihydro-1H-isoquinolin-2-yl]-propyl}-3-(2-methyl-quinolin-4-yl)-urea | 1.11 | 585.21 |
| 82 | 1-{3-[1-(3,4-Dimethoxy-benzyl)-6,8-dimethoxy-3,4-dihydro-1H-isoquinolin-2-yl]-propyl}-3-quinolin-4-yl-urea | 1.11 | 571.21 |
| 83 | 1-{3-[1-(4-Fluoro-benzyl)-6,7-dimethoxy-3,4-dihydro-1H-isoquinolin-2-yl]-propyl}-3-quinolin-4-yl-urea | 1.07 | 529.22 |
| 84 | 1-{2-[5-(3,4-Dimethoxy-benzyl)-7,8-dihydro-5H-[1,3]dioxolo[4,5-g]isoquinolin-6-yl]-ethyl}-3-pyridin-4-yl-urea | 0.99 | 491.09 |
| 85 | 1-{2-[5-(3,4-Dimethoxy-benzyl)-7,8-dihydro-5H-[1,3]dioxolo[4,5-g]isoquinolin-6-yl]-ethyl}-3-quinolin-4-yl-urea | 1.07 | 541.08 |
| 86 | 1-{2-[6-(3,4-Dimethoxy-benzyl)-2,3,8,9-tetrahydro-6H-[1,4]dioxino[2,3-g]isoquinolin-7-yl]-ethyl}-3-pyridin-4-yl-urea | 1.00 | 505.07 |
| 87 | 1-{2-[6-(3,4-Dimethoxy-benzyl)-2,3,8,9-tetrahydro-6H-[1,4]dioxino[2,3-g]isoquinolin-7-yl]-ethyl}-3-quinolin-4-yl-urea | 1.06 | 555.08 |
| 88 | 1-[2-(1-Benzhydryl-5,8-dimethoxy-3,4-dihydro-1H-isoquinolin-2-yl)-ethyl]-3-quinolin-4-yl-urea | 1.14 | 573.11 |
| 89 | 1-[2-(1-Benzhydryl-6,7-dimethoxy-3,4-dihydro-1H-isoquinolin-2-yl)-ethyl]-3-pyridin-4-yl-urea | 1.10 | 523.07 |
| 90 | 1-[2-(1-Benzhydryl-6,7-dimethoxy-3,4-dihydro-1H-isoquinolin-2-yl)-ethyl]-3-quinolin-4-yl-urea | 1.12 | 573.08 |
| 91 | 1-[2-(1-Benzyl-5,8-dimethoxy-3,4-dihydro-1H-isoquinolin-2-yl)-ethyl]-3-pyridin-4-yl-urea | 1.09 | 447.15 |
| 92 | 1-[2-(1-Benzyl-5,8-dimethoxy-3,4-dihydro-1H-isoquinolin-2-yl)-ethyl]-3-quinolin-4-yl-urea | 1.13 | 497.09 |
| 93 | 1-{2-[1-(3,4-Dimethoxy-benzyl)-5,8-dimethoxy-3,4-dihydro-1H-isoquinolin-2-yl]-ethyl}-3-quinolin-4-yl-urea | 1.11 | 557.08 |
| 94 | 1-{2-[1-(2,5-Dimethoxy-benzyl)-5,8-dimethoxy-3,4-dihydro-1H-isoquinolin-2-yl]-ethyl}-3-quinolin-4-yl-urea | 1.14 | 557.12 |
| 95 | 1-{2-[6,7-Dimethoxy-1-(1-phenyl-propyl)-3,4-dihydro-1H-isoquinolin-2-yl]-ethyl}-3-pyridin-4-yl-urea | 1.08 | 475.12 |
| 96 | 1-{2-[6,7-Dimethoxy-1-(1-phenyl-propyl)-3,4-dihydro-1H-isoquinolin-2-yl]-ethyl}-3-quinolin-4-yl-urea | 1.11 | 525.09 |
| 97 | 1-{2-[1-(3,4-Dimethoxy-benzyl)-6,7-dimethoxy-4,4-dimethyl-3,4-dihydro-1H-isoquinolin-2-yl]-ethyl}-3-quinolin-4-yl-urea | 1.29 | 585.29 |
| 98 | 1-{2-[(R)-1-(3,4-Dimethoxy-benzyl)-6,7-dimethoxy-3,4-dihydro-1H-isoquinolin-2-yl]-ethyl}-3-(2-methyl-quinolin-4-yl)-urea | 1.05 | 571.35 |
| 99 | 1-{2-[(R)-1-(3,4-Dimethoxy-benzyl)-6,7-dimethoxy-3,4-dihydro-1H-isoquinolin-2-yl]-ethyl}-3-quinolin-4-yl-urea | 1.01 | 557.14 |
| 100 | 1-{2-[(R)-1-(4-Fluoro-benzyl)-6,7-dimethoxy-3,4-dihydro-1H-isoquinolin-2-yl]-ethyl}-3-(2-methyl-quinolin-4-yl)-urea | 0.77 | 529.08 |
| 101 | 1-{2-[7-Benzyloxy-1-(3,4-dimethoxy-benzyl)-6-methoxy-3,4-dihydro-1H-isoquinolin-2-yl]-ethyl}-3-(2-methyl-quinolin-4-yl)-urea | 0.82 | 647.1 |
| 102 | 1-{2-[1-(3,4-Dimethoxy-benzyl)-6-methoxy-3,4-dihydro-1H-isoquinolin-2-yl]-ethyl}-3-(2-methyl-quinolin-4-yl)-urea | 0.77 | 541.13 |
| 103 | 1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid methylamide | 0.78 | 606.13 |
| 104 | 1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid propylamide | 0.82 | 634.04 |
| 105 | 1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid dimethylamide | 0.78 | 620.00 |

Example 106
1-{2-[1-(4-Fluoro-benzyl)-6,7-dimethoxy-3,4-dihydro-1H-isoquinolin-2-yl]-ethyl}-3-(7-methyl-[1,8]naphthyridin-4-yl)-urea

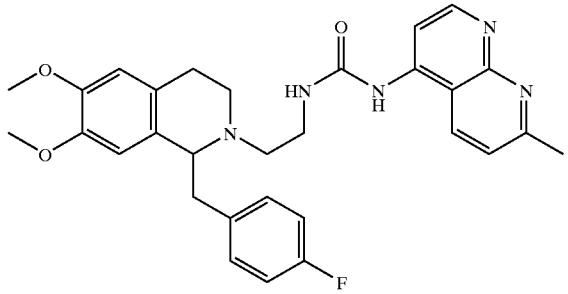

106.1. {2-[1-(4-Fluoro-benzyl)-6,7-dimethoxy-3,4-dihydro-1H-isoquinolin-2-yl]-ethyl}-carbamic Acid Tert-butyl Ester To a solution of 1-(4-fluorobenzyl)-6,7-dimethoxy-1,2,3,4-tetrahydro-isoquinoline (example A31, 1.05 g, 3.5 mmol) in THF (40 mL) is added (2-bromo-ethyl)-carbamic acid tert-butyl ester (example B1, 0.94 g, 4.2 mmol) and DIPEA. The reaction mixture is stirred at 70° C. in a sealed flask for 5 days. After cooling to rt, the reaction mixture is evaporated to dryness, and the residue is purified by preparative HPLC to provide the title compound.

106.2. 1-{2-[1-(4-Fluoro-benzyl)-6,7-dimethoxy-3,4-dihydro-1H-isoquinolin-2-yl]-ethy}-3-(7-methyl-[1,8]naphthyridin-4-yl)-urea To a stirred solution of {2-[1-(4-fluoro-benzyl)-6,7-dimethoxy-3,4-dihydro-1H-isoquinolin-2-yl]-ethyl}-carbamic acid tert-butyl ester (example 106.1, 0.22 g, 0.5 mmol) in glacial AcOH (1 mL) is added conc. HCl (0.1 mL). After 5 min, the reaction mixture is partitioned with CHCl$_3$ (20 mL) and 1 N NaOH (15 mL). The organic phase is evaporated. The residue is taken up in DMSO (2 mL) and treated with CDI (0.2 g, 0.6 mmol, 1.2 eq). The reaction mixture is stirred at rt for 3 h, and then 4-amino-7-methyl-[1,8]-naphthyridine (example C5, 0.19 g, 0.6 mmol) is added. To the resulting solution is added in a single portion NaHMDS (2 M in THF, 1.25 mL, 2.5 mmol). The reaction mixture is stirred at rt for 30 min, then H$_2$O (0.4 mL) is added. The reaction mixture is evaporated and the residue purified by preparative HPLC to provide the title compound.

LC-MS (MeCN/H$_2$O, 1:1) $t_R$=0.92 min, m/z=530.3 (M+1)

Example 107
1-{2-[1-(4-Fluoro-benzyl)-6,7-dimethoxy-3,4-dihydro-1H-isoquinolin-2-yl]-ethyl}-3-(5,6,7,8-tetrahydro-quinolin-4-yl)-urea

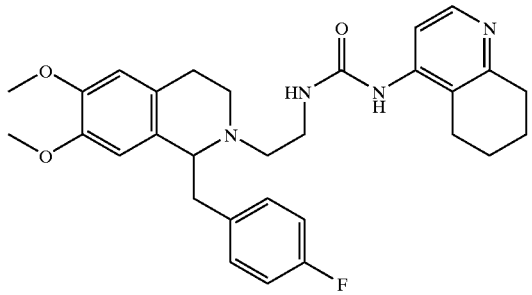

To a stirred solution of {2-[1-(4-fluoro-benzyl)-6,7-dimethoxy-3,4-dihydro-1H-isoquinolin-2-yl]-ethyl}-carbamic acid tert-butyl ester (example 106.1, 0.22 g, 0.5 mmol) in glacial AcOH (1 mL) is added conc. HCl (0.1 mL). After 5 min, the reaction mixture is partitioned between CHCl$_3$ (20 mL) and 1 N NaOH (15 mL). The organic phase is evaporated. The residue is taken up in DMSO (2 mL) and treated with CDI (0.2 g, 0.6 mmol, 1.2 eq). The reaction mixture is stirred at rt for 3 h, and then 4-amino-5,6,7,8-tetrahydroquinoline (example C4, 0.19 g, 0.6 mmol) is added. To the resulting solution is added in a single portion NaHMDS (2 M in THF, 1.25 mL, 2.5 mmol). The reaction mixture is stirred at rt for 30 min, then H$_2$O (0.4 mL) is added. The reaction mixture is evaporated and the residue purified by preparative HPLC to provide the title compound.

LC-MS (MeCN/H$_2$O, 1:1) $t_R$=0.92 min, m/z=519.3 (M+1)

Example 108
1-[2-(Benzyl-methyl-amino)-pyridin-4-yl]-3-{2-[1-(4-fluoro-benzyl)-6,7-dimethoxy-3,4-dihydro-1H-isoquinolin-2-yl]-ethyl}-urea

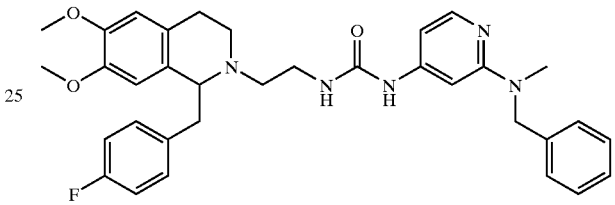

108.1 Benzyl-(4-isocyanato-pyridin-2-yl)-methyl-amine

To a solution of 2-(benzyl-methyl-amino)-isonicotinic acid (example C8, 780 mg, 3.2 mmol) in DMF (10 mL) at 0° C. is added triethylamine (360 mg, 3.5 mmol). After 5 minutes DPPA (975 mg, 3.5 mmol) is added, and stirring is continued for 2 h at 0° C. and 12 h at 20° C. The reaction is quenched with ice (10 g) and extracted with Et$_2$O (6×30 mL). The combined organic phases are washed successively with saturated NaHCO$_3$ (2×15 mL) and water (2×10 mL), and are evaporated without heating in vacuo. The residue is dissolved in dry toluene (16 mL) and heated to reflux for 2 h. The resulting solution is carried forward without further isolation of the title compound.

108.2 1-[2-(Benzyl-methyl-amino)-pyridin-4-yl]-3-{2-[1-(4-fluoro-benzyl)-6,7-dimethoxy-3,4-dihydro-1H-isoquinolin-2-yl]-ethyl}-urea To a stirred solution of {2-[1-(4-fluoro-benzyl)-6,7-dimethoxy-3,4-dihydro-1H-isoquinolin-2-yl]-ethyl}-carbamic acid tert-butyl ester (example 106.1, 0.22 g, 0.5 mmol) in CH$_2$Cl$_2$ (1 mL) is added TFA (1 mL). After 2 h, the reaction mixture evaporated and partitioned between CH$_2$Cl$_2$ (20 mL) and 1 N NaOH (15 mL). The organic phase is dried (MgSO$_4$) and evaporated. The residue is dissolved in CH$_2$Cl$_2$ (2 mL) and added to a freshly prepared solution of benzyl-(4-isocyanato-pyridin-2-ylmethyl-amine (example 108.1, 95.7 mg, 0.40 mmol) in toluene (2 mL). The mixture is stirred for 15 h at 20° C. Evaporation of the solvent and purification by HPLC provides the title compound.

LC-MS (MeCN/H$_2$O, 1:1) $t_R$=0.73 min, m/z=584.3 (M+1)

Examples 109–111

The additional examples set out in the following table are prepared starting from example 106.1 and examples C9 to C11 using the method of example 108.

| Example No | Example | $t_R$ | $[M + H]^+$ |
|---|---|---|---|
| 109 | 1-[2-(Benzyl-methyl-amino)-6-methyl-pyridin-4-yl]-3-{2-[1-(4-fluoro-benzyl)-6,7-dimethoxy-3,4-dihydro-1H-isoquinolin-2-yl]-ethyl}-urea | 0.76 | 598.43 |
| 110 | 1-{2-[1-(4-Fluoro-benzyl)-6,7-dimethoxy-3,4-dihydro-1H-isoquinolin-2-yl]-ethyl}-3-[2-(methyl-phenyl-amino)-pyridin-4-yl]-urea | 0.80 | 570.10 |
| 111 | 1-{2-[1-(4-Fluoro-benzyl)-6,7-dimethoxy-3,4-dihydro-1H-isoquinolin-2-yl]-ethyl}-3-(2-pyrrolidin-1-yl-pyridin-4-yl)-urea | 0.77 | 534.09 |

Example 112

1-{2-[1-(4-Fluoro-benzyl)-6,7-dimethoxy-3,4-dihydro-1H-isoquinolin-2-yl]-ethyl}-3-(2-methylamino-1-yl-pyridin-4-yl)-urea

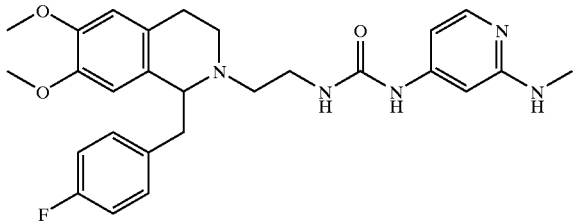

To a mixture of 1-[2-(benzyl-methyl-amino)pyridin-4-yl]-3{2-[1-(4-fluoro-benzyl)-6,7-dimethoxy-3,4-dihydro-1H-isoquinolin-2-yl]-ethyl}-urea (example 108, 0.12 g, 0.2 mmol) and Pd (10% on carbon, 20 mg) in MeOH (10 mL) is added HCl (1N, 0.2 mL). A stream of hydrogen is passed through the solution for 0.5 h and the solution is stirred under an atmosphere of hydrogen for 15 h. The solution is filtered and evaporated to provide the title compound.

LC-MS (MeCN/H$_2$O, 1:1) $t_R$=0.77 min, m/z=534.09 (M+1)

Example 113

(Quinolin-4-yl)-carbamic acid 2-(6.7-dimethoxy-1-phenethyl-3,4-dihydro-1H-isoquinolin-2-yl)-ethyl Ester

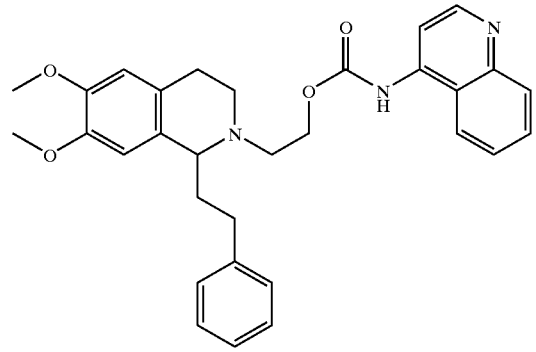

113.1. 2-(6,7-Dimethoxy-1-phenethyl-3,4-dihydro-1H-isoquinolin-2-yl)-ethanol

A solution of 6,7-dimethoxy-1-phenethyl-1,2,3,4-tetrahydro-isoquinoline (example A21, 59.5 mg, 0.2 mmol) and 2-bromoethanol (28.3 μL, 0.4 mmol) in tetrahydropyran (3 mL) is treated with DIPEA (68 μL, 0.4 mmol), and the reaction mixture is heated at 90° C. in a sealed flask for 5 days. The reaction is mixture evaporated to dryness, and the residue is purified by preparative HPLC, to provide the title compound.

113.2. (Quinolin-4-yl)-carbamic Acid 2-(6,7-dimethoxy-1-phenethyl-3,4-dihydro-1H-isoquinolin-2-yl)-ethyl Ester To a solution of 2-(6,7-dimethoxy-1-phenethyl-3,4-dihydro-1H-isoquinolin-2-yl)-ethanol (example 113.1, 29.7 mg, 0.087 mmol) in THF (1 mL) is added CDI (28.2 mg, 0.174 mmol, 2.0 eq). The reaction mixture is stirred at rt for 3 h, and then 4-amino-quinoline (example C3, 14 mg, 0.1 mmol) is added. To the resulting solution is added in a single portion NaHMDS (2 M in THF, 218 μL, 0.44 mmol). The reaction mixture is stirred at rt for 30 min, then H$_2$O/AcOH (9:1, 0.4 mL) is added. The reaction mixture is evaporated and the residue purified by preparative HPLC to provide the title compound.

LC-MS (MeCN/H$_2$O, 1:1) $t_R$=1.17 min, m/z=512.19 (M+1)

Examples 114–120

The additional examples set out in the following table are prepared starting from examples A1 to A52 and examples C1 to C3 using the method of example 113.

| Example No | Example | $t_R$ | $[M + H]^+$ |
|---|---|---|---|
| 114 | Quinolin-4-yl-carbamic acid 2-(1-benzyl-6,7-dimethoxy-3,4-dihydro-1H-isoquinolin-2-yl)-ethyl ester | 1.09 | 498.19 |
| 115 | Quinolin-4-yl-carbamic acid 2-[1-(4-fluoro-benzyl)-6,7-dimethoxy-3,4-dihydro-1H-isoquinolin-2-yl]-ethyl ester | 1.12 | 516.16 |
| 116 | Quinolin-4-yl-carbamic acid 3-(1-benzyl-6,7-dimethoxy-3,4-dihydro-1H-isoquinolin-2-yl)-propyl ester | 1.05 | 512.15 |
| 117 | Quinolin-4-yl-carbamic acid 3-(6,7-dimethoxy-1-phenethyl-3,4-dihydro-1H-isoquinolin-2-yl)-propyl ester | 1.10 | 526.19 |
| 118 | Quinolin-4-yl-carbamic acid 3-[1-(3,4-difluoro-benzyl)-6,7-dimethoxy-3,4-dihydro-1H-isoquinolin-2-yl]-propyl ester | 1.10 | 548.18 |

-continued

| Example No | Example | $t_R$ | $[M + H]^+$ |
|---|---|---|---|
| 119 | Quinolin-4-yl-carbamic acid 3-[1-(3,4-dimethoxy-benzyl)-6,8-dimethoxy-3,4-dihydro-1H-isoquinolin-2-yl]-propyl ester | 1.10 | 572.25 |
| 120 | Quinolin-4-yl-carbamic acid 3-[1-(4-fluoro-benzyl)-6,7-dimethoxy-3,4-dihydro-1H-isoquinolin-2-yl]-propyl ester | 1.08 | 530.12 |

Example 121

In Vitro Biological Characterization

The inhibitory activity of the compounds of general formula 1 on the actions of urotensin II can be demonstrated using the test procedures described hereinafter:

1) Inhibition of Human [125I]-urotensin II Binding to a Rhabdomyosarcoma Cell Line Whole cell binding of human [$^{125}$I]-urotensin II is performed using human-derived TE-671 rhabdomyosarcoma cells (Deutsche Sammlung von Mikroorganismen und Zellkulturen, cell line #ACC-263), by methods adapted from a whole cell endothelin binding assay (Breu V et al., In vitro characterization of Ro-46-2005, a novel synthetic non-peptide antagonist of $ET_A$ and $ET_B$ receptors. FEBS Lett. 1993, 334, 210–214).

The assay is performed in 250 μL Dubecco's modified eagle medium, pH 7.4 (GIBCO BRL, CatNo 31885-023), including 25 mM HEPES (Fluka, CatNo 05473), 1.0% DMSO (Fluka, CatNo 41644) and 0.5% (w/v) BSA Fraction V (Fluka, CatNo 05473) in polypropylene microtiter plates (Nunc, CatNo 442587). 300,000 suspended cells are incubated with gentle shaking for 4 h at 20° C. with 20 pM human [$^{125}$I]Urotensin II (Anawa Trading SA, Wangen, Switzerland, 2130 Ci/mmol) and increasing concentrations of unlabeled antagonist. Minimum and maximum binding are derived from samples with and without 100 nM unlabelled U-II, respectively. After the 4 h incubation period, the cells are filtered onto GF/C filter plates (Packard, CatNo 6005174). The filter plates are dried, and then 50 μL scintillation cocktail (Packard, MicroScint 20, CatNo 6013621) is added to each well. The filter plates are counted in a microplate counter (Packard Bioscience, TopCount NXT).

All test compounds are dissolved and diluted in 100% DMSO. A ten-fold dilution into assay buffer is performed prior to addition to the assay. The final concentration of DMSO in the assay is 1.0/, which is found not to interfere with the binding. IC50 values are defined as the concentration of antagonist inhibiting 50% of the specific binding of [$^{125}$I]human U-II. Specific binding is the difference between maximum binding and minimum binding, as described above. An IC50 value of 0.206 nM is found for unlabeled human U-II. The compounds of the invention are found to have IC50 values ranging from 1 to 10000 nM in this assay. Specific examples have IC50's given in the following table.

| Example | IC50 [nM] |
|---|---|
| 20 | 67 |
| 22 | 63 |
| 29 | 125 |
| 58 | 550 |

2) Inhibition of Human Urotensin II-Induced Contractions of Isolated Rat Aortic Arch Adult Wistar rats are anesthetized ($CO_2$ inhalation) and exsanguinated. The aortic arch is excised, dissected and cut in 3 rings of 3 mm, ring #1 being the more proximal and ring #3 being the more distal. Each ring is suspended in a 10 mL isolated organ bath filled with Krebs-Henseleit solution (in mM; NaCl 115, KCl 4.7, $MgSO_4$ 1.2, $KH_2PO_4$ 1.5, $NaHCO_3$ 25, $CaCl_2$ 2.5, glucose 10; pH 7.4) kept at 37° C. and gassed with 95% $O_2$ and 5% $CO_2$. The rings are connected to force transducers and isometric tension is recorded (EMKA Technologies SA, Paris, France). The rings are stretched to a resting tension of 3 g. Cumulative doses of human urotensin II ($10^{-11}$ M to $10^{-6}$ M) are added after a 20 min incubation with the test compound or its vehicle (DMSO, 10 μL). An EC50 value of 1.09±0.1 nM is found for unlabeled human U-II. The functional inhibitory potency of the test compound is assessed by calculating the pD$_2$' according to the formula: pD$_2$'=Log (CR-1)-Log [B], where CR is the ratio of the maximal effect without/with antagonist and [B] the concentration of the antagonist. Specific examples have pD2' values given in the following table:

| Example | pD2' |
|---|---|
| 29 | 5.23 |
| 93 | 5.45 |

What is claimed is:

1. A compound of the general formula 1,

General Formula 1

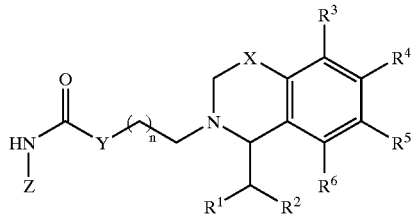

wherein

X represents —$CH_2$—, —$CH_2CH_2$—, —$C(CH_3)_2$—;

Y represents oxygen, NH;

n represents the numbers 1 or 2;

Z represents quinolin-4-yl which may be mono-substituted with lower alkyl in the positions 2, 6, or 8, or di-substituted with lower alkyl in the positions 2,6 or 2,8; [1,8]naphthyridin-4-yl which may be substituted in position 7 with lower alkyl; pyridin-4-yl which may be substituted in position 2 with $R^7R^8N$— and additionally in position 6 with hydrogen or lower alkyl;

$R^1$ represents naphthalen-1-yl; naphthalen-2-yl; benzo[1,3]dioxol-5-yl; benzyl, or mono-, di-, or tri-substituted benzyl substituted in the phenyl ring independently with lower alkyl, lower alkyloxy, trifluoromethyl, halogen, cyano; phenyl, or mono-, di- or tri-substituted phenyl, substituted independently with lower alkyl, lower alkyloxy, trifluoromethyl, halogen, cyano;

$R^2$ represents hydrogen, lower alkyl, aryl or forms with $R^1$ a styryl group of E or Z geometry, whereby the phenyl ring in the styryl group may be mono-, di- or tri-substituted phenyl, substituted independently with lower alkyl, lower alkyloxy, trifluoromethyl, halogen, cyano;

$R^3$, $R^4$, $R^5$ and $R^6$ independently represent hydrogen, cyano, hydroxy, lower alkyloxy, aralkyloxy, lower alkenyloxy, and $R^5$ additionally represents $R^7R^8NCO$;

$R^4$ and $R^5$ together may form with the phenyl ring a five- or a six-membered ring containing one or two oxygen atoms;

$R^7$ and $R^8$ independently represent hydrogen, lower alkyl, aryl, aralkyl, or together with the N form a pyrrolidine, piperidine, or morpholine ring;

and optically pure enantiomers or diastereomers, mixtures of enantiomers or diastereomers, diastereomeric racemates, and mixtures of diastereomeric racemates;

as well as their pharmaceutically acceptable salts, solvent complexes, and morphological forms.

2. A compound of general formula 2,

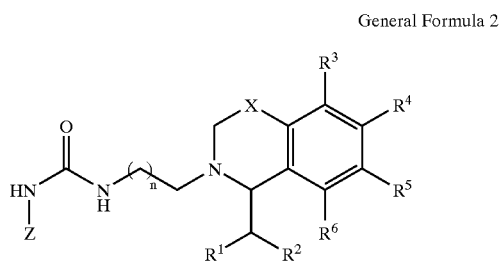

General Formula 2 wherein $R^1$, $R^2$, $R^3$, $R^4$, $R^5$, $R^6$, X, Z, and n have the meaning given in general formula 1 of claim 1.

3. A compound of general formula 3,

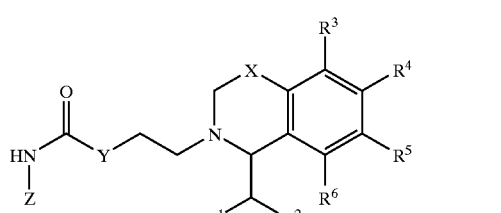

General Formula 3 wherein $R^1$, $R^2$, $R^3$, $R^4$, $R^5$, $R^6$, X, Y, and Z have the meaning given in general formula 1 of claim 1.

4. A compound of general formula 4,

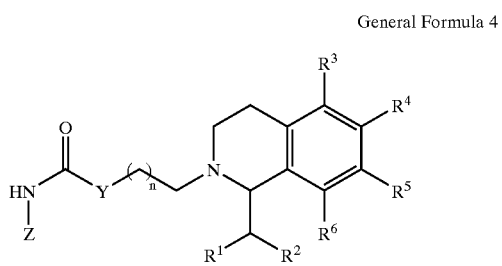

General Formula 4 wherein $R^1$, $R^2$, $R^3$, $R^4$, $R^5$, $R^6$, Y, Z, and n have the meaning given in general formula 1 of claim 1.

5. A compound of general formula 5,

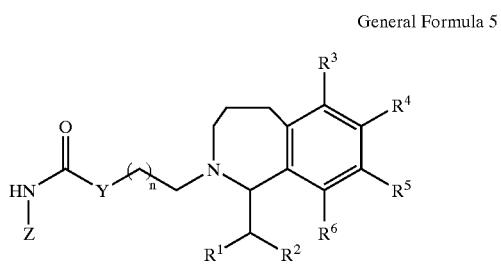

General Formula 5 wherein $R^1$, $R^2$, $R^3$, $R^4$, $R^5$, $R^6$, Y, Z, and n have the meaning given in general formula 1 of claim 1.

6. A compound of general formula 6,

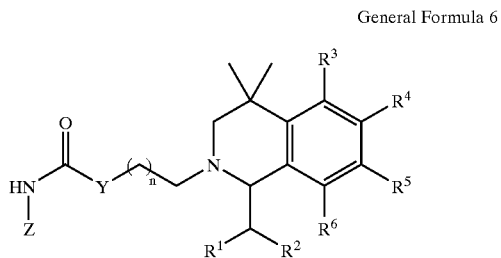

General Formula 6 wherein

R1, R2, R3, R4, R5, R6, Y, Z, and n have the meaning given in general formula 1 of claim 1.

7. A compound of general formula 7,

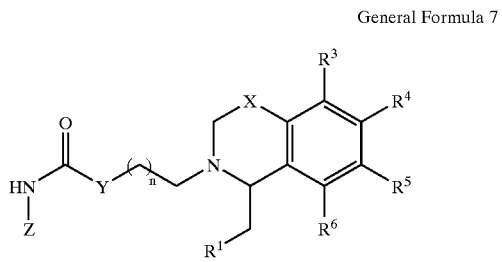

General Formula 7 wherein

R1, R3, R4, R5, R6, X, Y, Z, and n have the meaning given in general formula 1 of claim 1.

8. A compound of general formula 8,

General Formula 8

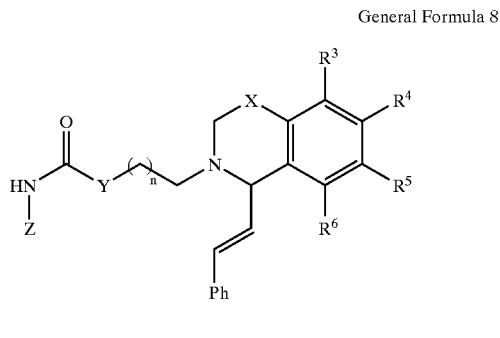

wherein

Ph is phenyl; mono-, di- or tri-substituted phenyl, substituted independently with hydrogen, lower alkyl, lower alkyloxy, trifluoromethyl, halogen, or cyano;

$R^3$, $R^4$, $R^5$, $R^6$, X, Y, Z, and n have the meaning given in general formula 1 of claim 1.

9. A compound of general formula 9,

General Formula 9

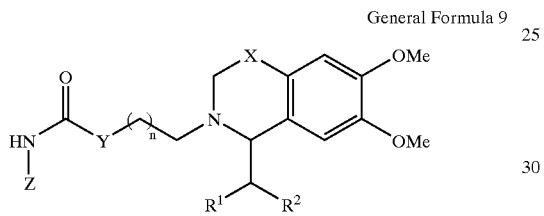

wherein

R1, R2, X, Y, Z, and n have the meaning given in general formula 1 of claim 1.

10. A compound of general formula 10,

General Formula 10

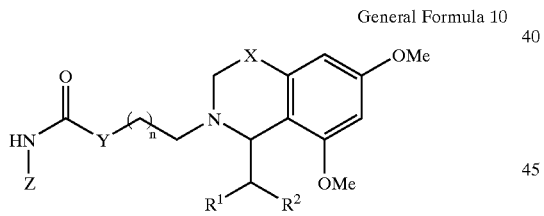

wherein

R1, R2, X, Y, Z, and n have the meaning given in general formula 1 of claim 1.

11. A compound of general formula 11,

General Formula 11

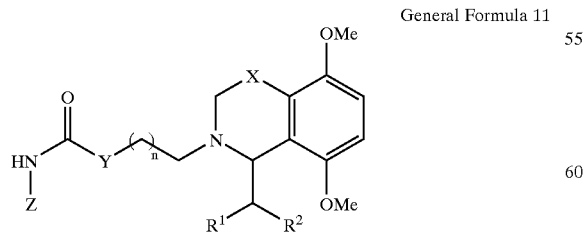

wherein

R1, R2, X, Y, Z, and n have the meaning given in general formula 1 of claim 1.

12. A compound of general formula 12,

General Formula 12

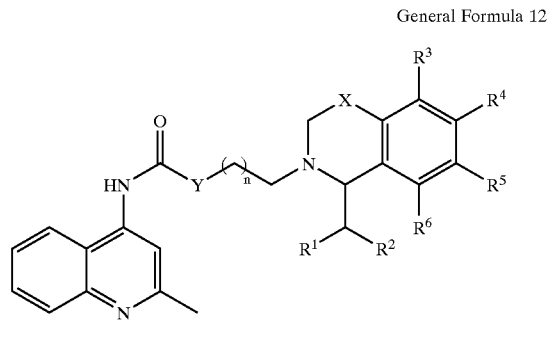

wherein

R1, R2, R3, R4, R5, R6, X, Y, and n have the meaning given in general formula 1 of claim 1.

13. A compound of general formula 13,

General Formula 13

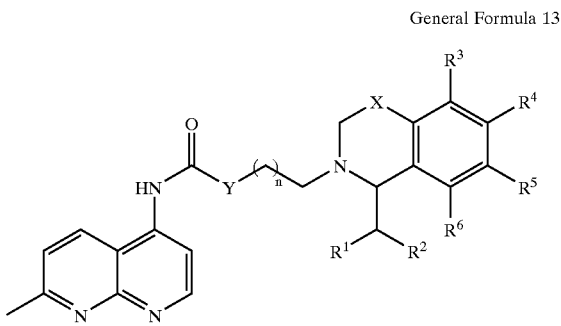

wherein

R1, R2, R3, R4, R5, R6, X, Y, and n have the meaning given in general formula 1 of claim 1.

14. A compound of general formula 14,

General Formula 14

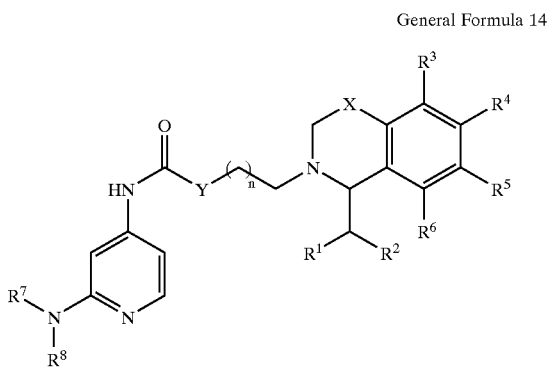

wherein

R1, R2, R3, R4, R5, R6, R7, R8, X, Y, and n have the meaning given in general formula 1 of claim 1.

15. A compound of general formula 15,

General Formula 15

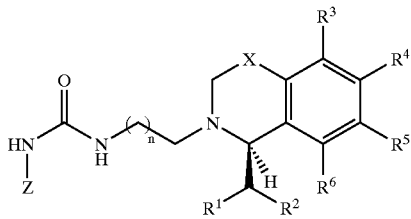

wherein
the 1 position of the 1,2,3,4-tetrahydroisoquinoline ring system has the R absolute stereochemical configuration;
R1, R2, R3, R4, R5, R6, X, Z, and n have the meaning given in general formula 1 of claim 1.

16. A compounds of general formula 16,

General Formula 16

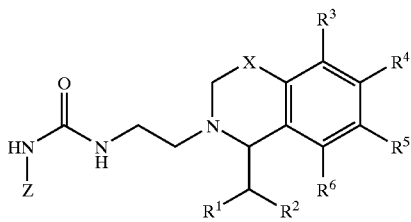

wherein
R3, R4, R5, and R6 are independently hydrogen or lower alkyloxy;
R1, R2, and Z have the meaning given in general formula 1 of claim 1.

17. The compounds according to claim 1 selected from the group consisting of
1-{2-[1-(4-Fluoro-benzyl)-6,8-dimethoxy-3,4-dihydro-1H-isoquinolin-2-yl]-ethyl}-3-(2-methyl-quinolin-4-yl)-urea;
1-{2-[1-(3,4-Difluoro-benzyl)-6,8-dimethoxy-3,4-dihydro-1H-isoquinolin-2-yl]-ethyl}-3-(2-methyl-quinolin-4-yl)-urea;
1-{2-[1-(3-Fluoro-4-methoxy-benzyl 6,8-dimethoxy-3,4-dihydro-1H-isoquinolin-2-yl]-ethyl}-3-(2-methyl-quinolin-4-yl)-urea;
1-{2-[1-(3,4-Difluoro-benzyl)-6,8-dimethoxy-3,4-dihydro-1H-isoquinolin-2-yl-ethyl}-3-quinolin-4-yl-urea;
1-{2-[1-(3-Fluoro methoxy-benzyl)-6,8-dimethoxy-3,4-dihydro-1H-isoquinolin-2-yl]-ethyl}-3-quinolin-4-yl-urea;
1-{2-[1-(4-Fluoro-benzyl)-6,8-dimethoxy-3,4-dihydro-1H-isoquinolin-2-yl]-ethyl}-3-quinolin-4-yl-urea;
1-(2-{1-[2-(4-Fluoro-phenyl)-ethyl]-6,8-dimethoxy-3,4-dihydro-1H-isoquinolin-2-yl}-ethyl)-3-(2-methyl-quinolin-4-yl)-urea;
1-(2-{1-[2-(2,4-Difluoro-phenyl)-ethyl]-6,8-dimethoxy-3,4-dihydro-1H-isoquinolin-2-yl}-ethyl)-3-(2-methyl-quinolin-4-yl)-urea;
1-(2-{1-[2-(2,4-Difluoro-phenyl)-ethyl]-6,8-dimethoxy-3,4-dihydro-1H-isoquinolin-2-yl}-ethyl)-3-quinolin-4-yl-urea;
1-(2-{1-[2-(3,4-Difluoro-phenyl)-ethyl]-6,8-dimethoxy-3,4-dihydro-1H-isoquinolin-2-yl}-ethyl)-3-(2-methyl-quinolin-4-yl)-urea;
1-(2-{1-[2-(3,4-Difluoro-phenyl)-ethyl]-6,8-dimethoxy-3,4-dihydro-1H-isoquinolin-2-yl}-ethyl)-3-quinolin-4-yl-urea;
1-(2-{1-[2-(4-Fluoro-phenyl)-ethyl]-6,8-dimethoxy-3,4-dihydro-1H-isoquinolin-2-yl}-ethyl)-3-quinolin-4-yl-urea;
1-{2-[1-(4-Fluoro-benzyl)-6,7-dimethoxy-3,4-dihydro-1H-isoquinolin-2-yl]-ethyl}-3-(2-methyl-quinolin-4-yl)-urea;
1-{2-[1-(3,4-Dimethoxy-benzyl)-7,8-dimethoxy-1,3,4,5-tetrahydro-benzo[c]azepin-2-yl]-ethyl}-3-(2-methyl-quinolin-4-yl)-urea;
1-(2-{1-[(E)-2-(2,4-Difluoro-phenyl)vinyl]-6,7-dimethoxy-3,4-dihydro-1H-isoquinolin-2-yl}-ethyl)-3-(2-methyl-quinolin-4-yl)-urea;
1-(2-{1-[(E)-2-(2,5-Difluoro-phenyl)-vinyl]-6,7-dimethoxy-3,4-dihydro-1H-isoquinolin-2-yl}-ethyl)-3-(2-methyl-quinolin-4-yl)-urea;
1-(2-{1-[2-(2,3-Dfluoro-phenylyethyl]-6,7-dimethoxy-3,4-dihydro-1H-isoquinolin-2-yl}-ethyl)-3-(2-methyl-quinolin-4-yl)-urea;
1-(2-{1-[2-(2,4-Difluoro-phenyl)-ethyl]-6,7-dimethoxy-3,4-dihydro-1H-isoquinolin-2-yl}-ethyl)-3-(2-methyl-quinolinyl)-urea;
1-(2-{1-[2-(2,5-Bis-trifluoromethyl-phenyl)-ethyl]-6,7-dimethoxy-3,4-dihydro-1H-isoquinolin-2-yl}-ethyl)-3-(2-methyl-quinolin-4-yl)-urea;
1-(2-{1-[2(2,5-Difluoro-phenyl)-ethyl]-6,7-dimethoxy-3,4-dihydro-1H-isoquinolin-2-yl}-ethyl)-3-(2-methyl-quinolin-4-yl)-urea;
1-(2-{1-[2-(3,4-Difluoro-phenyl)-ethyl]-6,7-dimethoxy-3,4-dihydro-1H-isoquinolin-2-yl}-ethyl)-3-(2-methyl-quinolin-4-yl)-urea;
1-(2-{1-[2-(3,4-Dimethoxy-phenyl)-ethyl]-6,7-dimethoxy-3,4-dihydro-1H-isoquinolin-2-yl}-ethyl)-3-(2-methyl-quinolin-4-yl)-urea;
1-(2-{1-[2-(3,5-Bis-trifluoromethyl-phenyl ethyl]-6,7-dimethoxy-3,4-dihydro-1H-isoquinolin-2-yl}-ethyl)-3-(2-methyl-quinolin-4-yl)-urea;
1-(2-{1-[2-(4-Fluoro-phenyl)ethyl]-6,7-dimethoxy-3,4-dihydro-1H-isoquinolin-2-yl}-ethyl)-3-(2-methyl-quinolin-4-yl)-urea;
1-(2-{6,7-Dimethoxy-1-[2-(2-methoxy-phenyl)-ethyl]-3,4-dihydro-1H-isoquinolin-2-yl}-ethyl)-3-(2-methyl-quinolinyl)-urea;
1-(2-{6,7-Dimethoxy-1-[2-(3-methoxy-phenyl)-ethyl]-3,4-dihydro-1H-isoquinolin-2-yl}-ethyl)-3-(2-methyl-quinolin-4-yl)-urea;
1-(2-{6,7-Dimethoxy-1-[2-(4-methoxy-phenyl)-ethyl]-3,4-dihydro-1H-isoquinolin-2-yl}-ethyl)-3-(2-methyl-quinolin-4-yl)-urea;
1-(2-{6,7-Dimethoxy-1-[2-(4-trifluoromethyl-phenyl) ethyl]-3,4-dihydro-1H-isoquinolin-2-yl}-ethyl)-3-(2-methyl-quinolin-4-yl)-urea;
1-[2-(6,7-Dimethoxy-1-phenethyl-3,4-dihydro-1H-isoquinolin-2-yl)-ethy]-3-(2-methyl-quinolin-4-yl)-urea;
1-[2-(6,7-Dimethoxy-1-phenethyl-3,4-dihydro-1H-isoquinolin-2-yl)ethyl]-3-pyridin-4-yl-urea;
1-[2-(6,7-Dimethoxy-1-phenethyl-3,4-dihydro-1H-isoquinolin-2-yl)-ethyl]-3-quinolin-4-yl-urea;

1-[3-(6,7-Dimethoxy-1-phenethyl-3,4-dihydro-1H-isoquinolin-2-yl)-propyl]-3-(2-methyl-quinolin-4-yl)-urea;

1-[3-(6,7-Dimethoxy-1-phenethyl-3,4-dihydro-1H-isoquinolin-2-yl)-propyl]-3-quinolin-4-yl-urea;

1-[2-(1-Benzo[1,3]dioxol-5-ylmethyl-6,7-dimethoxy-3,4-dihydro-1H-isoquinolin-2-yl)-ethyl]-3-(2-methyl-quinolin-4-yl)-urea;

1-[2-(1-Benzo[1,3]dioxol-5-ylmethyl-6,7-dimethoxy-3,4-dihydro-1H-isoquinolin-2-yl)ethyl]-3-pyridin-4-yl-urea;

1-[2-(1-Benzo[1,3]dioxol-5-ylmethyl-6,7-dimethoxy-3,4-dihydro-1H-isoquinolin-2-yl)-ethyl]-3-quinolin-4-yl-urea;

1-[2-(1-Benzyl-3,4-dihydro-1H-isoquinolin-2-yl)-ethyl]-3-pyridin-4-yl-urea;

1-[2-(1-Benzyl-3,4-dihydro-1H-isoquinolin-2-yl)-ethyl]-3-quinolin-4-yl-urea;

1-[2-(1-Benzyl-6,7-dimethoxy-3,4-dihydro-1H-isoquinolin-2-yl)-ethyl]-3-(2-methyl-quinolin-4-yl)-urea;

1-[2-(1-Benzyl-6,7-dimethoxy-3,4-dihydro-1H-isoquinolin-2-yl)-ethyl]-3-pyridin-4-yl-urea;

1-[2-(1-Benzyl-6,7-dimethoxy-3,4-dihydro-1H-isoquinolin-2-yl)-ethyl]-3-quinolin-4-yl-urea;

1-[2-(1-Benzyl-6-methoxy-3,4-dihydro-1H-isoquinolin-2-yl)-ethyl]-3-pyridin-4-yl-urea;

1-[2-(1-Benzyl-6-methoxy-3,4-dihydro-1H-isoquinolin-2-yl)-ethyl]-3-quinolin-4-yl-urea;

1-[2-(6,7-Dimethoxy-1-naphthalen-2-ylmethyl-3,4-dihydro-1H-isoquinolin-2-yl)-ethyl]-3-pyridin-4-yl-urea;

1-[2-(6,7-Dimethoxy-1-naphthalen-2-ylmethyl-3,4-dihydro-1H-isoquinolin-2-yl)-ethyl]-3-quinolin-4-yl-urea;

1-[2-(6,7-Dimethoxy-1-phenoxymethyl-3,4-dihydro-1H-isoquinolin-2-yl)-ethyl]-3-pyridin-4-yl-urea;

1-[3-(1-Benzyl-6,7-dimethoxy-3,4-dihydro-1H-isoquinolin-2-yl)-propyl]-3-(2-methyl-quinolin-4-yl)-urea;

1-[3-(1-Benzyl-6,7-dimethoxy-3,4-dihydro-1H-isoquinolin-2-yl)-propyl]-3-quinolin-4-yl-urea;

1-{2-[1-(2,5-Dimethoxy-benzyl)-6,7-dimethoxy-3,4-dihydro-1H-isoquinolin-2-yl]-ethyl}-3-pyridin-4-yl-urea;

1-{2-[1-(2,5-Dimethoxy-benzyl)-6,7-dimethoxy-3,4-dihydro-1H-isoquinolin-2-yl]-ethyl}-3-quinolin-4-yl-urea;

1-{2-[1-(2,6-Dichloro-benzyl)-6,7-dimethoxy-3,4-dihydro-1H-isoquinolin-2-yl]-ethyl}-3-(2-methyl-quinolin-4-yl)-urea;

1-{2-[1-(3,4-Difluoro-benzyl)-6,7-dimethoxy-3,4-dihydro-1H-isoquinolin-2-yl]-ethyl}-3-pyridin-4-yl-urea;

1-{2-[1-(3,4-Difluoro-benzyl)-6,7-dimethoxy-3,4-dihydro-1H-isoquinolin-2-yl]-ethyl}-3-quinolin-4-yl-urea;

1-{2-[1-(3,4-Dimethoxy-benzyl)-6,7,8-trimethoxy-3,4-dihydro-1H-isoquinolin-2-yl]-ethyl}-3-quinolin-4-yl-urea;

1-{2-[1-(3,4-Dimethoxy-benzyl)-6,7-dimethoxy-3,4-dihydro-1H-isoquinolin-2-yl]-ethyl}-3-pyridin-4-yl-urea;

1-{2-[1-(3,4-Dimethoxy-benzyl)-6,7-dimethoxy-3,4-dihydro-1H-isoquinolin-2-yl]-ethyl}-3-quinolin-4-yl-urea;

1-{2-[1-(3,4-Dimethoxy-benzyl)-6,7-dimethoxy-3,4-dihydro-1H-isoquinolin-2-yl]-ethyl}-3-(5,6,7,8-tetrahydro-quinolin-4-yl)-urea;

1-{2-[1-(3,4-Dimethoxy-benzyl)-6,8-dimethoxy-3,4-dihydro-1H-isoquinolin-2-yl]-ethyl}-3-(2-methyl-quinolin-4-yl)-urea;

1-{2-[1-(3,4-Dimethoxy-benzyl)-6,8-dimethoxy-3,4-dihydro-1H-isoquinolin-2-yl]-ethyl}-3-pyridin-4-yl-urea;

1-{2-[1-(3,4-Dimethoxy-benzyl)-6,8-dimethoxy-3,4-dihydro-1H-isoquinolin-2-yl]-ethyl}-3-quinolin-4-yl-urea;

1-{2-[1-(3,4-Dimethoxy-benzyl)-6-methoxy-3,4-dihydro-1H-isoquinolin-2-yl]-ethyl}-3-pyridin-4-yl-urea;

1-{2-[1-(3,4-Dimethoxy-benzyl)-6-methoxy-3,4-dihydro-1H-isoquinolin-2-yl]-ethyl}-3-quinolin-4-yl-urea;

1-{2-[1-(3-Fluoro-4-methoxy-benzyl)-6,7-dimethoxy-3,4-dihydro-1H-isoquinolin-2-yl]-ethyl}-3-(2-methyl-quinolin-4-yl)-urea;

1-{2-[1-(3-Fluoro-5-trifluoromethyl-benzyl)-6,7-dimethoxy-3,4-dihydro-1H-isoquinolin-2-yl]-ethyl}-3-(2-methyl-quinolin-4-yl)-urea;

1-{2-[1-(4-Chloro-benzyl)-6,7-dimethoxy-3,4-dihydro-1H-isoquinolin-2-yl]-ethyl}-3-pyridin-4-yl-urea;

1-{2-[1-(4-Chloro-benzyl)-6,7-dimethoxy-3,4-dihydro-1H-isoquinolin-2-yl]-ethyl}-3-quinolin-4-yl-urea;

1-{2-[1-(4-Fluoro-benzyl)-6,7-dimethoxy-3,4-dihydro-1H-isoquinolin-2-yl]-ethyl}-3-pyridin-4-yl-urea;

1-{2-[1-(4-Fluoro-benzyl)-6,7-dimethoxy-3,4-dihydro-1H-isoquinolin-2-yl]-ethyl}-3-quinolin-4-yl-urea;

1-{2-[6,7-Dimethoxy-1-(2,3,4-trimethoxy-benzyl)-3,4-dihydro-1H-isoquinolin-2-yl]-ethyl}-3-pyridin-4-yl-urea;

1-{2-[6,7-Dimethoxy-1-(2,3,4-trimethoxy-benzyl)-3,4-dihydro-1H-isoquinolin-2-yl]-ethyl}-3-quinolin-4-yl-urea;

1-{2-[6,7-Dimethoxy-1-(3,4,5-trimethoxy-benzyl)-3,4-dihydro-1H-isoquinolin-2-yl]-ethyl}-3-(2-methyl-quinolinyl)-urea;

1-{2-[6,7-Dimethoxy-1-(3,4,5-trimethoxy-benzyl)-3,4-dihydro-1H-isoquinolin-2-yl]-ethyl}-3-pyridinyl-urea;

1-{2-[6,7-Dimethoxy-1-(3,4,5-trimethoxy-benzyl)-3,4-dihydro-1H-isoquinolin-2-yl]-ethyl}-3-quinolin-4-yl-urea;

1-{2-[6,7-Dimethoxy-1-(3-methoxy-benzyl)-3,4-dihydro-1H-isoquinolin-2-yl]-ethyl}-3-pyridin-4-yl-urea;

1-{2-[6,7-Dimethoxy-1-(3-methoxy-benzyl)-3,4-dihydro-1H-isoquinolin-2-yl]-ethyl}-3-quinolin-4-yl-urea;

1-{2-[6,7-Dimethoxy-1-(4-methoxy-benzyl)-3,4-dihydro-1H-isoquinolin-2-yl]-ethyl}-3-pyridin-4-yl-urea;

1-{2-[6,7-Dimethoxy-1-(4-methoxy-benzyl)-3,4-dihydro-1H-isoquinolin-2-yl]-ethyl}-3-quinolin-4-yl-urea;

1-{3-[1-(3,4-Difluoro-benzyl)-6,7-dimethoxy-3,4-dihydro-1H-isoquinolin-2-yl]-propyl}-3-quinolin-4-yl-urea;

1-{3-[1-(3,4-Dimethoxy-benzyl)-6,7-dimethoxy-3,4-dihydro-1H-isoquinolin-2-yl]-propyl}-3-(2-methyl-quinolin-4-yl)-urea;

1-{3-[1-(3,4-Dimethoxy-benzyl)-6,7-dimethoxy-3,4-dihydro-1H-isoquinolin-2-yl]-propyl}-3-quinolin-4-yl-urea;

1-{3-[1-(3,4-Dimethoxy-benzyl)-6,8-dimethoxy-3,4-dihydro-1H-isoquinolin-2-yl]-propyl}-3-(2-methyl-quinolin-4-yl)-urea;

1-{3-[1-(3,4-Dimethoxy-benzyl)-6,8-dimethoxy-3,4-dihydro-1H-isoquinolin-2-yl]-propyl}-3-quinolin-4-yl-urea;

1-{3-[1-(4-Fluoro-benzyl)-6,7-dimethoxy-3,4-dihydro-1H-isoquinolin-2-yl]-propyl}-3-quinolin-4-yl-urea;

1-{2-[5-(3,4-Dimethoxy-benzyl)-7,8-dihydro-5H-[1,3]dioxolo[4,5-g]isoquinolin-6-yl]-ethyl}-3-pyridin-4-yl-urea;

1-{2-[5-(3,4-Dimethoxy-benzyl)-7,8-dihydro-5H-[1,3]dioxolo[4,5-g]isoquinolin-6-yl]-ethyl}-3-quinolin-yl-urea;

1-{2-[6-(3,4-Dimethoxy-benzyl)-2,3,8,9-tetrahydro-6H-[1,4]dioxino[2,3-g]isoquinolin-7-yl]-ethyl}-3-pyridin-4-yl-urea;

1-{2-[6-(3,4-Dimethoxy-benzyl)-2,3,8,9-tetrahydro-6H-[1,4]dioxino[2,3-g]isoquinolin-7-yl]-ethyl}-3-quinolin-4-yl-urea;

1-[2-(1-Benzhydryl-5,8-dimethoxy-3,4-dihydro-1H-isoquinolin-2-yl)-ethyl]-3-quinolin-4-yl-urea;

1-[2-(1-Benzhydryl-6,7-dimethoxy-3,4-dihydro-1H-isoquinolin-2-yl)-ethyl]-3-pyridin-4-yl-urea;

1-[2-(1-Benzhydryl-6,7-dimethoxy-3,4-dihydro-1H-isoquinolin-2-yl)-ethyl]-3-quinolin-4-yl-urea;

1-[2-(1-Benzyl-5,8-dimethoxy-3,4-dihydro-1H-isoquinolin-2-yl)-ethyl]-3-pyridin-4-yl-urea;

1-[2-(1-Benzyl-5,8-dimethoxy-3,4-dihydro-1H-isoquinolin-2-yl)ethyl]-3-quinolin-4-yl-urea;

1-{2-[1-(3,4-Dimethoxy-benzyl)-5,8-dimethoxy-3,4-dihydro-1H-isoquinolin-2-yl]-ethyl}-3-quinolin-4-yl-urea;

1-{2-[1-(2,5-Dimethoxy-benzyl)-5,8-dimethoxy-3,4-dihydro-1H-isoquinolin-2-yl]-ethyl}-3-quinolin-4-yl-urea;

1-{2-[6,7-Dimethoxy-1-(1-phenyl-propyl)-3,4-dihydro-1H-isoquinolin-2-yl]-ethyl}-3-pyridin-4-yl-urea;

1-{2-[6,7-Dimethoxy-1-(1-phenyl-propyl)-3,4-dihydro-1H-isoquinolin-2-yl]-ethyl}-3-quinolin-4-yl-urea;

1-{2-[1-(3,4-Dimethoxy-benzyl)-6,7-dimethoxy-4,4-dimethyl-3,4-dihydro-1H-isoquinolin-2-yl]-ethyl}-3-quinolin-4-yl-urea;

1-{2-[(R)-1-(3,4-Dimethoxy-benzyl)-6,7-dimethoxy-3,4-dihydro-1H-isoquinolin-2-yl]-ethyl}-3-(2-methyl-quinolin-4-yl)-urea;

1-{2-[(R)-1-(3,4-Dimethoxy-benzyl)-6,7-dimethoxy-3,4-dihydro-1H-isoquinolin-2-yl]-ethyl}-3-quinolin-4-yl-urea;

1-{2-[(R)-1-(4-Fluoro-benzyl)-6,7-dimethoxy-3,4-dihydro-1H-isoquinolin-2-yl]-ethyl}-3-(2-methyl-quinolin-4-yl)-urea;

1-{2-[7-Benzyloxy-1-(3,4-dimethoxy-benzyl)-6-methoxy-3,4-dihydro-1H-isoquinolin-2-yl]-ethyl}-3-(2-methyl-quinolin-4-yl)-urea;

1-{2-[1-(3,4-Dimethoxy-benzyl)-6-methoxy-3,4-dihydro-1H-isoquinolin-2-yl]-ethyl}-3-(2-methyl-quinolin-4-yl)-urea;

1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid methylamide;

1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid propylamide;

1-(3,4-Dichloro-benzyl)-6-methoxy-2-{2-[3-(2-methyl-quinolin-4-yl)-ureido]-ethyl}-1,2,3,4-tetrahydroisoquinoline-7-carboxylic acid dimethylamide;

1-{2-[1-(4-Fluoro-benzyl)-6,7-dimethoxy-3,4-dihydro-1H-isoquinolin-2-yl]-ethyl}-3-(7-methyl-[1,8]naphthyridin-4-yl)-urea;

1-{2-[1-(4-Fluoro-benzyl)-6,7-dimethoxy-3,4-dihydro-1H-isoquinolin-2-yl]-ethyl}-3-(5,6,7,8-tetrahydro-quinolin-4-yl)-urea;

1-[2-(Benzyl-methyl-amino)-pyridinyl-4-yl]-3-{2-[1-(4-fluoro-benzyl)-6,7-dimethoxy-3,4-dihydro-1H-isoquinolin-2-yl]-ethyl}-urea;

1-[2-(Benzyl-methyl-amino)-6-methyl-pyridin-4-yl]-3-{2-[1-(4-fluoro-benzyl)-6,7-dimethoxy-3,4-dihydro-1H-isoquinolin-2-yl]-ethyl}-urea;

1-{2-[1-(4-Fluoro-benzyl)-6,7-dimethoxy-3,4-dihydro-1H-isoquinolin-2-yl]-ethyl}-3-[2-(methyl-phenyl-amino)-pyridinyl]-urea;

1-{2-[1-(4-Fluoro-benzyl)-6,7-dimethoxy-3,4-dihydro-1H-isoquinolin-2-yl]-ethyl}-3-(2-pyrrolidin-1-yl-pyridin-4-yl)-urea;

1-{2-[1-(4-Fluoro-benzyl)-6,7-dimethoxy-3,4-dihydro-1H-isoquinolin-2-yl]-ethyl}-3-(2-methylamino-1-yl-pyridin-4-yl)-urea;

Quinolin-4-yl-carbamic acid 2-(6,7-dimethoxy-1-phenethyl-3,4-dihydro-1H-isoquinolin-2-yl)-ethyl ester;

Quinolin-4-yl-carbamic acid 2-(1-benzyl-6,7-dimethoxy-3,4-dihydro-1H-isoquinolin-2-yl)-ethyl ester;

Quinolin-4-yl-carbamic acid 2-[1-(4-fluoro-benzyl)-6,7-dimethoxy-3,4-dihydro-1H-isoquinolin-2-yl]-ethyl ester;

Quinolin-4-yl-carbamic acid 3-(1-benzyl-6,7-dimethoxy-3,4-dihydro-1H-isoquinolin-2-yl)-propyl ester;

Quinolin-4-yl-carbamic acid 3-(6,7-dimethoxy-1-phenethyl-3,4-dihydro-1H-isoquinolin-2-yl]-propyl ester;

Quinolin-4-yl-carbamic acid 3-[1-(3,4-difluoro-benzyl)-6,7-dimethoxy-3,4-dihydro-1H-isoquinolin-2-yl]-propyl ester;

Quinolinyl-carbamic acid 3-[1-(3,4-dimethoxy-benzyl)-6,8-dimethoxy-3,4-dihydro-1H-isoquinolin-2-yl]-propyl ester; and Quinolin-4-yl-carbamic acid 3-[1-(4-fluoro-benzyl)-6,7-dimethoxy-3,4-dihydro-1H-isoquinolin-2-yl]-propyl ester;

and pharmaceutically acceptable salts thereof.

18. A Pharmaceutical composition comprising a compound of claim 1 and a pharmaceutically acceptable carrier and/or and adjuvant.

* * * * *